United States Patent [19]
Ojima et al.

[11] Patent Number: 5,811,452
[45] Date of Patent: Sep. 22, 1998

[54] TAXOID REVERSAL AGENTS FOR DRUG-RESISTANCE IN CANCER CHEMOTHERAPY AND PHARMACEUTICAL COMPOSITIONS THEREOF

[75] Inventors: Iwao Ojima, Stony Brook; Ralph J. Bernacki, Elma, both of N.Y.

[73] Assignees: The Research Foundation of State University of New York, Albany; Health Research Inc, Buffalo, both of N.Y.

[21] Appl. No.: 780,633

[22] Filed: Jan. 8, 1997

[51] Int. Cl.$^6$ .................. A61K 31/335; C07D 305/14
[52] U.S. Cl. ...................... 514/449; 549/510; 549/511
[58] Field of Search ..................... 549/510, 511; 514/449

[56] References Cited

U.S. PATENT DOCUMENTS

| | | | |
|---|---|---|---|
| 5,264,591 | 11/1993 | Bombardelli et al. | 549/214 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,350,866 | 9/1994 | Holton et al. | 549/510 |
| 5,475,011 | 12/1995 | Ojima et al. | 514/320 |

OTHER PUBLICATIONS

Ojima, et al., "A New Paclitaxel Photoaffinity Analog with a 3-(4-Benzoylphenyl)propanoyl Probe for Characterization of Drug-Binding Sites on Tubulin and P-Glycoprotein," *Journal of Medicinal Chemistry*, vol. 38, No. 20 (1995).

Kobayashi, et al., "Taxuspines A~C, New Taxoids from Japanese *Yew Taxus Cuspidata* Inhibition Drug Transport Activity of P-Glycoprotein in Multidrug-Resistant Cells," *Tetrahedron*, vol. 50, No. 25, pp. 7401–7416 (1994).

*Primary Examiner*—Ba K. Trinh
*Attorney, Agent, or Firm*—Hoffman & Baron, LLP

[57] ABSTRACT

The present invention is directed to novel taxoids possessing strong reversing activities for drug-resistance associated with anti-cancer agents, the preparation of these reversal agents and pharmaceutical compositions thereof. The new taxoids of the present invention have the formula (I).

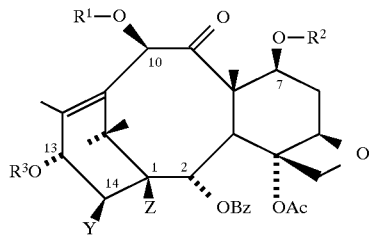

19 Claims, No Drawings

TAXOID REVERSAL AGENTS FOR DRUG-RESISTANCE IN CANCER CHEMOTHERAPY AND PHARMACEUTICAL COMPOSITIONS THEREOF

This work was in part supported by a grant from the National Institutes of Health (GM42798 and CA13038).

FIELD OF INVENTION

The present invention relates to new taxoids possessing strong reversing activities for drug-resistance associated with anticancer agents, the preparation of these reversal agents, and pharmaceutical compositions thereof.

BACKGROUND OF THE INVENTION

Clinical drug resistance is a serious obstacle in any cancer chemotherapy. Although the cause of this drug resistance is complex, it has been shown that multi-drug resistance (MDR) observed in tumor models is the major cause of the clinical drug resistance, at least for several types of common cancers including breast cancer [Sikic B. I. "Modulation of Multidrug Resistance: At the Threshold", J. Clin. Oncol., 1993, 11, 1629–1635]. Multi-drug resistance (MDR) is defined as cross-resistance to various structurally different cytotoxic (antitumor) agents, which is caused by increased outward transport of these agents through the plasma membrane by the action of P-glycoprotein as described by Sikic, B. I. in "Modulation of Multidrug Resistance: At the Threshold", J, Clin. Oncol., 11, 1629–1635, 1993. In other words, P-glycoprotein is over-expressed (mdr1 gene) in MDR cancer cells, which binds to cytotoxic (antitumor) agents and pumps them out. Several "reversal agents", i.e., MDR modulators, have been found such as cyclosporin A (immunodepressant) and verapamil (antihypertensive). Although these agents were not specially designed nor developed for the modulation of MDR, combined therapy with MDR-related antitumor agents with a modulator indeed shrinks tumors and prolongs life span in animal models. Modified versions of these agents, i.e., cyclosporin D (SDZ PSC 833) and dexverapamil, have been developed, which have recently shown some promising results in human clinical trails as discussed by Sikic, B. I. in "Modulation of Multidrug Resistance: At the Threshold", J. Clin. Oncol., 11, 1629–1635, 1993; and in Anti-Cancer Drugs, 5, Supplement 1, pp 58–73 1995; featuring "1st International Conference on Reversal of Multidrug Resistance in Cancer". It appears that the reversal agents also referred to as MDR modulators bind to P-glycoprotein and increase the accumulation and retention of anticancer drugs, thereby providing a biochemical and/or pharmacological basis for their action.

Cells that express mdr1 are found to be cross-resistant to anthracyclines, vinca alkaloids, podophyllotoxins, and taxanes. Among these drugs, it has been shown that Taxol® (paclitaxel) demonstrates highest degree of cross-resistance in MDR cells. Taxol® and Taxotere® (docetaxel) are currently considered among the most exciting drugs in cancer chemotherapy as more specifically described in "Taxane Anticancer Agents: Basic Science and Current Status", by George, G. I.; Chen, T. T.; Ojima, I.; Vyas, D. M. (EDs.), ACS Symp Ser. 583, American Chemical Society, Washington, D.C., 1995. Taxol® and Taxotere® possesses high cytotoxicity and strong antitumor activity against different cancers which have not been effectively treated by existing anticancer drugs. In 1992 FDA approval was obtained for Taxol® for the treatment of advanced ovarian cancer and in 1994 for treatment of metastatic breast cancer. FDA approval was also obtained for Taxotere® for the treatment of breast cancer in 1996. However, clinical drug resistance has already been observed and will become a difficult problem to overcome when the usage of these drugs increases. Such drug resistance has been a serious problem for the use of anthracyclines such as daunorubicin, doxorubicin, and idarubicin, vinca alkaloids such as vincristine, vinblastine, navelbine, podophyllotoxins such as etoposide and teniposide, and dactinomycin. Consequently, it is extremely important to discover and develop efficient reversal agents for MDR so that clinical oncologists can continue treatment of cancer patients with available anticancer drugs, including Taxol® and Taxotere®.

Kobayashi et al. recently reported that non-crytotoxic taxanes 1–4 isolated from the Japanese yew. *Taxus cuspidata Sieb et Zucc*, show strong effects on the accumulation of vincristine in MDR cells which are better than those of verapamil in "Taxuspines A~C, New Taxoids from Japanese Yew *Taxus Cuspidata* Inhibiting Drug Transport Activity of P-Glycoprotein in Multidrug-resistant Cells", Kobayashi, J. et al. Tetrahedron, 25, 7401–7416, 1994.

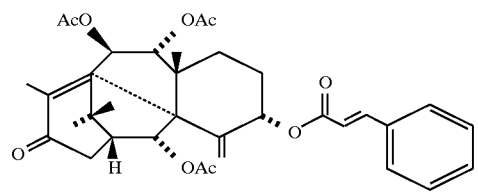

1

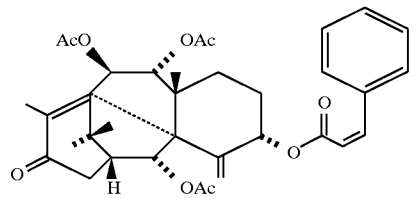

2

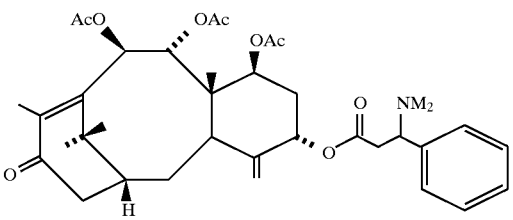

3

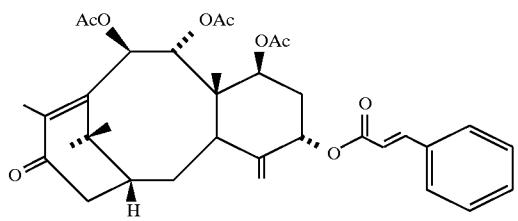

4

During our research on the development of new taxoid antitumor agents and their photoaffinity labels, we synthesized SB-T-5101. SB-T-5101 binds to microtubules as expected, but it has also been found that this compound binds to P-glycoprotein in Taxol-resistant cells (T1 cells) as well as vinblastine-resistant cells which are also cross-resistant to Taxol (V1 cells): SB-T-5101 binds to both mdr 1a (major) and mdr 1b (minor) in T1 cells, but it only binds to mdr 1b in V1 cells as shown by Ojima, I., et al. in "A New Paclitaxel Photoaffinity Analog with a 3-(4-benzoylphenyl) propanoyl Probe for Characterization of Drug-Binding Sites on Tubulin and P-Glycoprotein." J. Med. Chem. 38, 3891–3894, 1995. It should be noted that SB-T-5101 does not bind to other proteins, and thus no photoaffinity labeling is observed for non-drug resistant J7 (parent) cells.

In a preferred embodiment in formula I, whenever $R^1$ is $R^7$, $R^7$ is not H.

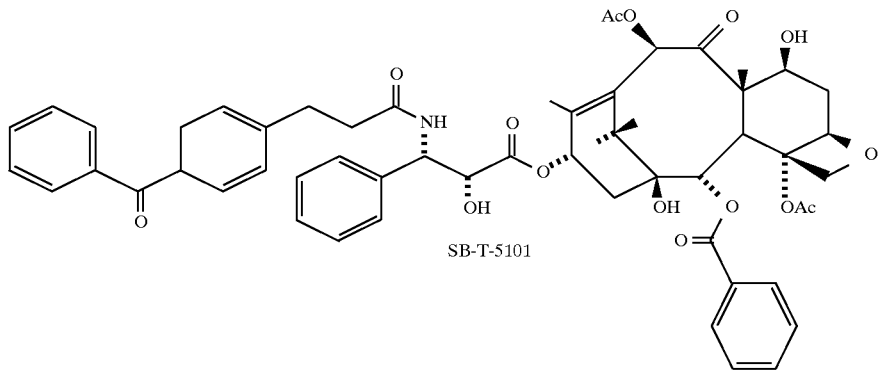

SB-T-5101

Accordingly, it is an objective of the present invention to develop new and efficient reversal agents for multi-drug resistance (MDR) in cancer cells and tumors based on the taxoid skeleton.

It is a further object of the present invention to develop reversal agents which will prevent multidrug resistance associated with the use of anthracyclines, Taxol®, Taxotere®, vinblastine and vincristine.

SUMMARY OF THE INVENTION

The present invention which addresses the needs of the prior art, provides compound of the formula (I).

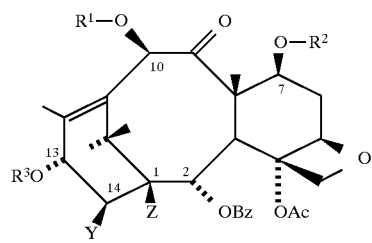

wherein
$R^1$, $R^2$ or $R^3$ represents a radical of the formula $R^4$—(A)$_k$—($R^5$)$_m$—(B)$_n$ or $R^7$;
$R^4$ is a substituted or unsubstituted alkyl, alkenyl, aryl, heteroaryl or alicyclic radical;
A is an oxygen, sulfur, or —$NR^6$— radical in which $R^6$ is a hydrogen or $R^4$;
$R^5$ is a substituted or unsubstituted alkylidene, alkenylidene, alkynylidene radical;
B is a carbonyl, —OC(O)— or —$NR^6$— radical;
k, m, and n are numbers selected from 0 and 1, however, k, m, and n are not 0 at the same time;
$R^7$ is a hydroxy protecting group, an acyl, carbomoyl, N-substituted carbamoyl or N, N-disubstituted carbamoyl radical or a hydrogen;
wherein $R^1$, $R^2$, and $R^3$ are not $R^7$ at the same time and $R^1$, $R^2$ and $R^3$ are not H at the same time;
Y is a hydrogen, a hydroxyl, or $R^1O$— radical wherein R1 is defined above;
Z is a hydroxyl radical;
Y and Z can be connected to form a cyclic structure.
Compounds of the formula I are useful as reversal agents for drug-resistance in cancer chemotherapy.

The new taxoids for formula (I) are synthesized by the modification of naturally occurring 10 -deacetylbaccatin III (II) and 14β-hydroxyl-10-deacetylbaccatin III (III).

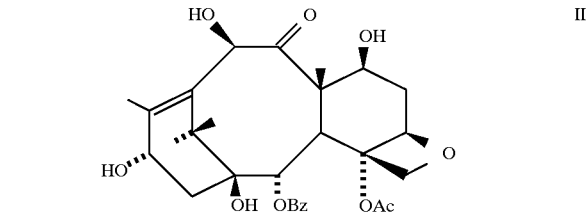

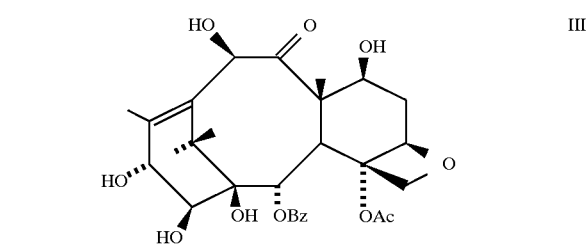

In another embodiment $R^1$ represents a radical of the formula $R^{4\#}$—(A)$_k$—($R^5$)$_m$—(B)$_n$, wherein $R^{4\#}$ is an aryl or heteroaryl radical substituted by one or more hydrophobic groups, cycloalkyl, cycloalkenyl, polycycloalkyl, polycycloalkenyl, polycyclic aryl, or polycyclic heteroaryl radical.

$R^4$ represents a straight chain or branched alkyl radical containing 1 to 10 carbon atoms, a straight chain or branched alkenyl radical containing 2 to 10 carbon atoms, or a straight chain or branched alkenyl radical containing 2 to 20 carbon atoms, a cycloalkyl radical containing 3 to 10 carbon atoms, a heterocycloalkyl radical containing 3 to 10 carbon atoms, a cycloalkenyl radical containing 3 to 10 carbon atoms, a heterocycloalkenyl radical containing 3 to 10 carbon atoms, a polycycloalkyl radical containing 6 to 20 carbon atoms, an aryl radical containing 6 to 20 carbons, a heteroaryl radical containing 3 to 20 carbon atoms; these radicals being optionally substituted with one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl the alkyl portion of which containing 1 to 15 carbon atoms, aryloxycarbonyl the aryl portion of which containing 6 to 20 carbon atoms, or heteroaryloxycarbonyl the heteroaryl portion of which containing 3 to 15 carbon atoms;

R⁵ is a straight chain or branched alkylidene, alkenylidene, alkynylidene radical containing 1 to 15 carbons;

R⁶ is a hydrogen or R⁴;

R⁷ is a hydroxy protecting group, an acyl radical containing 1 to 20 carbons, carbamoyl group, N-substituted carbamoyl radical containing 1 to 20 carbons, or N,N-disubstituted carbamoyl radical containing 2 to 40 carbon.

R⁴ can also be an alkyl radical selected from methyl, ethyl, propyl, isopropyl, butyl, isobutyl, tert-butyl, pentyl, isopentyl, neopentyl, hexyl, heptyl, octyl, nonyl, decyl, cyclohexylmethyl, cyclohexylethyl, benzyl, phenylethyl, cyclopropyl, cyclobutyl, cyclopentyl, cyclohexyl, cycloheptyl, cyclooctyl, and adamantyl, or an alkenyl radical selected from ethenyl, propenyl, butenyl, pentenyl, hexenyl, heptenyl, octenyl, nonenyl, decenyl, 2-phenylethenyl, 2-furylethenyl, 2-pyrrolylethenyl, 2-pyridylethenyl, 2-thienylethyl, or an an unsubstituted or substituted alkynyl radical selected from ethynyl, propynyl, butynyl, pentynyl, hexynyl, heptynyl, octynyl, nonynyl, decynyl, or an aryl radical selected from phenyl tolyl, methoxyphenyl dimethoxyphenyl, fluorophenyl, trifluoromethylphenyl, chlorophenyl, dimethylaminophenyl, chlorophenyl, acetylphenyl, pivaloylphenyl, benzoylphenyl, methoxylcarbonylphenyl, tert-butoxycarbonylphenyl, naphthyl, methoxynaphthyl, chloronaphthyl, acetylnaphthyl, benzoylnaphthyl, anthracenyl, phenanthrenyl, or a heteroaryl radical selected from furyl, pyrrolyl, pyridyl, thienyl, benzofuryl, benzopyrrolyl, benzothienyl, quinolinyl, indolyl, N-acetylindolyl, N-methylindolyl, N-allylindolyl, or a cycloalkenyl radical selected from cyclopropyl, cyclopentenyl, cyclohexenyl and cycloheptenyl, or a heterocycloalkyl selected from oxiranyl, pyrrolidinyl, piperidinyl, morpholinyl, tetrahydrofuryl, and tettrahydropyranyl, or a heterocycloalkenyl radical selected from dihydrofuryl, dihydropyrrolyl, dihydropiranyl, dihydropyridyl;

R⁶ is a hydrogen or R⁴.

$(A)_k$—$(R^5)_m$—$(B)_n$ is an α-, β-, or ω-hydroxyalkanoic acid residue, α-, β-, or ω-mercaptoalkanoic acid residue, or α-, β-, or ω-amino acid residue, wherein k=n=1 or ω-hydroxyalkyl, ω-mercaptoalkyl, or ω-aminoalkyl residue, wherein k=1 and n=0.

R⁴ can also be selected from benzoylphenyl, naphthyl, phenoxyphenyl, methoxyphenyl, ethoxyphenyl, isopropoxyphenyl, tert-butoxyphenyl, anthracenyl, phenathrenyl, isopropylphenyl, tert-butylphenyl, trimethylsilylphenyl;

$(A)_k$—$(R^5)_m$—$(B)_n$ is a hydroxyalkanoic acid residue selected from hydroxyacetyl, hydroxypropyl, and hydroxybutyl, or a mercaptoalkanoic acid residue selected from mercaptoacetyl, mercaptopropanoyl, mercaptobutanoyl, or an amino acid residue selected from, glycinyl, alanyl, β-alanyl, 4-aminobutanoyl, valyl, leucyl, isoleucyl, methionyl, phenylalanyl, tryptophanyl.

R⁷ is also a hydroxyl protecting group selected from methoxylmethyl (MOM), methoxyethyl (MEM), 1-ethoxyethyl (EE), benzyloxymethyl, (β-trimethylsilylethoxyl)methyl, tettrahydropyranyl, 2,2,2-trichloroethoxylcarbonyl (troc), benzyloxycarbonyl (Cbz), tert-butoxycarbonyl (t-Boc), 9-fluorenylmethoxycarbonyl (Fmoc), 2,2,2-trichloroethoxymethyl, trimethylsilyl, triethylsilyl (TES), tripropylsilyl, dimethylethylsilyl, (tert-butyl) dimethylsilyl (TBS), diethylmethylsilyl, dimethylphenylsilyl and diphenylmethylsilyl, or an acyl radical selected from acetyl, chloroacetyl, dichloroacetyl, trichloroacetyl, trifluoroacetyl, propanoyl, butanoyl, pentanoyl, hexanoyl, heptanoyl, cyclohexanecarbonyl, octanoyl, nonanoyl, decanoyl, undecanoyl, dodecanoyl, benzoyl, phenylacetyl, naphthalenecarbonyl, indoleacetyl, cyclopropanecarbonyl, fluorobenzoyl, chlorobenzoyl, azidobencyol, 2-propenoyl, 2-butenoyl, 2-methyl-1-propenoyl, 2-methyl-2-butenoyl, 3-methyl-2-butenoyl readical, or an N-substituted or N,N-disubstituted carbamoyl radical selected from N-methylcarbamoyl, N-ethylcarbamoyl, N-propylcarbamoyl, N-isopropylcarbamoyl, N-butylcarbamoyl, N-pentylcarbamoyl, N-hexylcarbamoyl, N,N-diemthylcarbamoyl, N,N-diethylcarbamoyl, N,N-dipropylcarbamoyl, N,N-dibutylcarbamoyl, pyrrolidine-N-carbonyl, piperidine-N-carbonyl, morpholine-N-carbonyl.

Y and Z are connected to form a carbonate, thiocarbonate, sulfate, sufite, ketal, or acetal.

R¹, R² or R³ is selected from 3-(benzolyphenyl)-2-propenoyl, 3-naphthyl-2-propenoyl, 3-biphenyl-2-propenoyl, 3-(phenoxyphenyl)-2-propenoyl, 3-(methoxyphenyl)-2-propenoyl, 3-(ethoxyphenyl)-2-propenoyl, 3-(isopropoxyphenyl)-2-propenoyl, 3-(tert-butoxyphenyl)-2-propenoyl, 3-(isopropylphenyl)-2-propenoyl, 3-(tert-butylphenyl)-2-propenoyl, 3-(trimethylsilylphenyl)-2-propenoyl, 3-anthracenyl-2-propenoyl, 3-phenanthrenyl-2-propenoyl, (benzoylphenyl)acetyl, naphthylacetyl, indoeacetyl, (N-acetyl)indoleacetyl, 3-(benzoylphenyl)propanoyl, 3-naphthylpropanoyl, 3-(biphenyl)propanoyl, 3-(phenoxyphenyl)propanoyl, 3-(methoxyphenyl)propanoyl, 3-(ethoxyphenyl)propanoyl, 3 -(isopropoxyphenyl)propanoyl, 3-tert-butoxyphenyl)propanoyl, 3-(isopropylphenyl)propanoyl, 3-(tert-butylphenyl)propanoyl, 3-(trimethylsilylphenyl)propanoyl, 4-(benzoylphenyl)butanoyl, 4-naphthylbutanoyl, 5-(benzoylphenyl)pentanoyl, 5-naphthylpentanoyl, 6-(benzoylphenyl)hexanoyl, 6-naphthylhexanoyl, 3-(anthracenyl)propanoyl, 4-(anthracenyl)butanoyl, 5-(anthracenyl)pentanoyl, 6-(anthracenyl)hexanoyl, 3-(phenanthrenyl)propanoyl, 4-(phenanthrenyl)butanoyl, 5-(phenanthrenyl)pentanoyl, 6-(phenanthrenyl)hexanoyl, (benzoylphenyl)methyl, naphthylmethyl, 2-(benzoylphenyl) ethyl, 3-(benzoylphenyl)propyl, 3-naphthylpropyl, 4-(benzoylphenyl)butyl, 4-naphthylbutyl, 5-(benzoylphenyl)pentyl, 5-naphthylpentyl, 6-(benzoylphenyl)hexyl, 6-naphthylhexyl, 3-(anthracenyl) propyl, 4-(anthracenyl)butyl, 5-(anthracenyl)pentyl, 6-(anthracenyl)hexyl, 3-(phenanthrenyl)propyl, 4-(phenanthrenyl)butyl, 5-(phenanthrenyl)pentyl, 6-(phenanthrenyl)hexyl.

Y is an R¹O radical;

R¹ is selected from 3-(benzoylphenyl)-2-propenoyl, 3-naphthyl-2-propenoyl, 3-biphenyl-2-propenoyl, 3-(phenoxyphenyl)-2-propenoyl, 3-(methoxyphenyl)-2-propenoyl, 3-(ethoxyphenyl)-2-propenoyl, 3-(isopropoxyphenyl)-2-propenoyl 3-(tert-butoxyphenyl)-2-propenoyl, 3-(isopropylphenyl)-2-propenoyl, 3-(tert-butylphenyl)-2-propenoyl, 3-(trimethylsilylphenyl)-2-propenoyl, 3-anthracenyl-2-propenoyl, 3-phenanthrenyl-2-propenoyl, (benzoylphenyl)acetyl, naphthylacetyl, indoleacetyl, (N-acetyl)indoleacetyl, 3-(benzoylphenyl) propanoyl, 3-naphthylpropanoyl, 3-(biphenyl)propanoyl, 3-(phenoxyphenyl)propanoyl, 3-(methoxyphenyl) propanoyl, 3-(ethoxyphenyl)propanoyl, 3-(isopropoxyphenyl)propanoyl, 3-(tert-butoxyphenyl) propanoyl, 3-(isopropylphenyl)propanoyl, 3-(tert-butylphenyl)propanoyl, 3-(trimethylsilylphenyl)propanoyl, 4-(benzoylphenyl)butanoyl, 4-naphthylbutanoyl, 5-(benzoylphenyl)pentanoyl, 5-naphthylpentanoyl, 6-(benzoylphenyl)hexanoyl, 6-naphthylhexanoyl, 3-(anthracenyl)propanoyl, 4-(anthracenyl)butanoyl, 5-(anthracenyl)pentanoyl, 6-(anthracenyl)hexanoyl, 3-(phenanthrenyl)propanoyl, 4-(phenanthrenyl)butanoyl, 5-(phenanthrenyl)pentanoyl, 6-(phenanthrenyl)hexanoyl, (benzoylphenyl)methyl, naphthylmethyl, 2-(benzoylphenyl)ethyl, 3-(benzoylphenyl)propyl, 3-naphthylpropyl, 4-(benzoylphenyl)butyl, 4-naphthylbutyl, 5-(benzoylphenyl)pentyl, 5-naphthylpentyl, 6-(benzoylphenyl)hexyl, 6-naphthylhexyl, 3-(anthracenyl)propyl, 4-(anthracenyl)butyl, 5-(anthracenyl)pentyl, 6-(anthracenyl)hexyl, 3-(phenanthrenyl)propyl, 4-(phenanthrenyl)butyl, 5-(phenanthrenyl)pentyl, 6-(phenanthrenyl)hexyl;

Z is a hydroxyl radical.

$R^1$, $R^2$ or $R^3$ is selected from 3-(4-benzoylphenyl)-2-propenoyl, 3-(4-benzoylphenyl)propanoyl, 3-(2-naphthyl)-2-propenoyl, and 3-(2-naphthyl)propanoyl.

$R^1$, $R^2$ or $R^3$ is selected from 3-(4-benzoylphenyl)-2-propenoyl, 3-(4-benzoylphenyl)propanoyl, 3-(2-naphthyl)-2-propenoyl, and 3-(2-naphthyl)propanoyl;

Y and Z are connected to form a carbonate, thiocarbonate, sulfate, sufite, ketal, or acetal.

$R^1$ and $R^2$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^3$ is a hydrogen or an acetyl radical;

Y is a hydrogen;

Z is a hydroxyl radical.

$R^1$ and $R^2$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^3$ is a hydrogen or an acetyl radical;

Y and Z are connected to form a carbonate, thiocarbonate, sulfate, sufite, ketal, or acetal.

$R^1$ and $R^3$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^2$ is a hydrogen or an acetyl radical;

Y is a hydrogen;

Z is a hydroxyl radical $R^2$ and $R^3$ are selected from 3-(4-benzoylphenyl-2-propenoyl, 3-(4-benzoylphenyl)propanoyl, 3-(2-naphthyl)-2-propenoyl, and 3-(2-naphthyl)propanoyl;

$R^1$ is a hydrogen or an acetyl radical;

Y is a hydrogen;

Z is a hydroxyl radical.

$R^1$, $R^2$ and $R^3$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

Y is a hydrogen;

Z is a hydroxyl radical

The new taxoids of the present invention have shown strong drug-resistance reversal activity when used as a pharmaceutical composition with antrarydins, Taxol®, Taxotere®, vinblastine and vincristine.

Methods for treating tumors which include administrating to a patient an effective amount of paclitaxel or doxorubicin with an effective amount of drug-resistance reversal compound of of the formula I are also encompassed by the present invention. The multi-drug resistance agents of the present invention have been found to be particularly useful when treating tumors selected from the group consisting of leukemia, melanoma, breast, non-small cell lung, ovarian, renal and colon cancers.

For a better understanding of the present invention, together with other and further objects, reference is made to the following description and its scope will be pointed out in the appended claims.

DETAILED DESCRIPTION OF THE INVENTION

New taxoids of the formula (I) hereinabove are useful as reversal agents for drug-resistance in cancer chemotherapy. These taxoids posses strong reversing activities against drug-resistant cancer cells to convert them to drug-sensitive cancer cells so that coadministration of an anticancer agent with a reversal agent of the present invention provides an efficient treatment for such drug-resistant tumors.

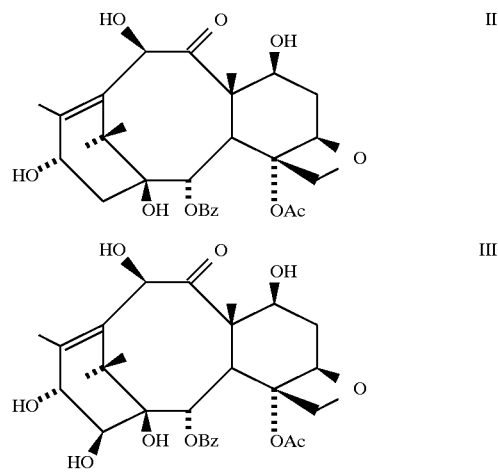

The new taxoids of formula I are synthesized by the modification of naturally occurring 10-deacetylbaccatin III (II) and 14β-hydroxyl-10-deacetylbaccatin III (III) through transformations illustrated in SCHEMES 1–12.

Scheme 1

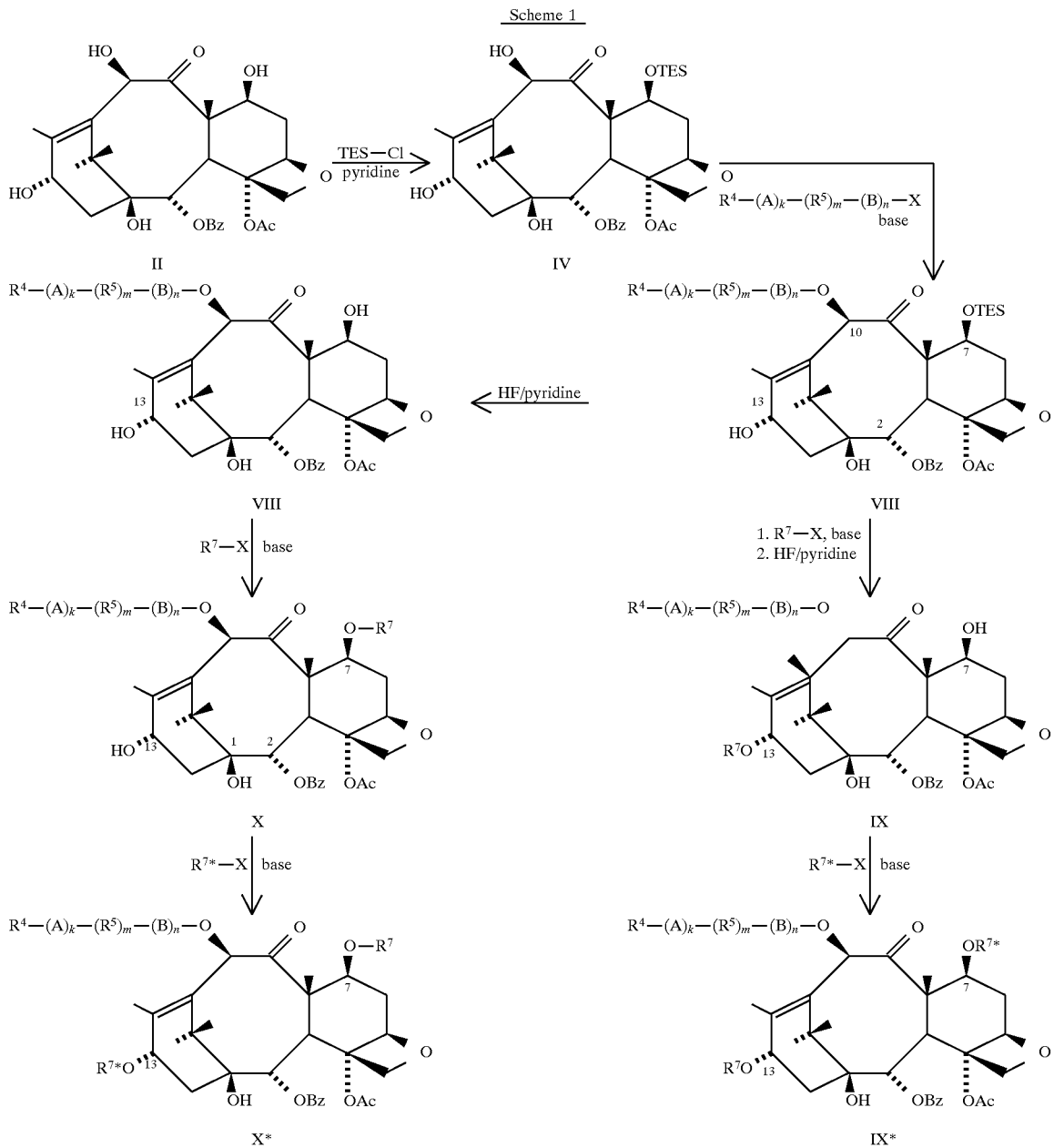

As Scheme 1 above illustrates, 10-deacetylbaccatin III (II) is readily converted to 7-TES-10-deacetylbaccatin III (IV) (TES=triethylsilyl) in high yield following the literature procedure described by Ojima, I. et al., in "New and Efficient Approaches to the Semisynthesis of Taxol and Its C-13 Side Chain Analogs by Means of β-Lactam Synthon Method," Tetrahedron, 48, 6985–7012 1992 and; Mangatal, L. et al., in "Application of the Vicinal Oxyamination Reaction with Asymmetric Induction to the Hemisynthesis of Taxol and Analogues," Tetrahedron, 45, 4177–4190, 1989, the content of which is incorporated herein by reference as is set forth in full. The C-10 hydroxyl group is modified by reacting with $R^4$—$(A)_k$—$(R^5)_m$—$(B)_n$—X, typically in the presence of a base such as 4-dimethylaminopyridine (DMAP), lithium hexamethyldisilazide (LiHMDS), lithium diisopropylamide (LDA) to give compound VII. $R^4$, $R^5$, A, B, k, m, and n defined above. X represents a halogen, hydroxyl, acyloxy, tosyloxy, mesyloxy, trifluoromethansulfonyl oxy, N-oxysuccinimide, and other leaving groups, which will be eliminated after the modification.

The $R^4$—$(A)_k$—$(R^5)_m$—$(B)_n$—X modifiers have typically carboxylic acid, acid chloride, alkyl halide, carboxylic anhydride, or activated ester terminus. Triethylsilyl group at C-7 is readily removed by HF/pyridine to afford VIII. The C-7 position is easily modified by $R^7$—X, in which $R^7$ and X are defined above, typically in the presence of a base such as 4-dimethylaminopyridine (DMAP), lithium hexamethyldisilazide (LiHMDS), lithium diisopropylamide (LDA) to yield X. This modification is specific to the C-7 position because of the substantial difference in the reactivity of the C-7 and C-13 hydroxyl groups in that the C-7 hydroxyl is much more reactive than the C-13 hydroxyl group. The hydroxyl group at C-1 does not have appreciable reactivity with alkylating and acylating agents. The C-13 position of VII is also readily modified with $R^7$—X, followed by deprotection with HF/pyridine to give IX.

position affords XV which has two hydrophobic tethers at C-7 and C-13. $R^{4'}$, $R^{5'}$, A', and B' simply indicate that each of these components is selected from $R^4$, $R^5$, A, and B

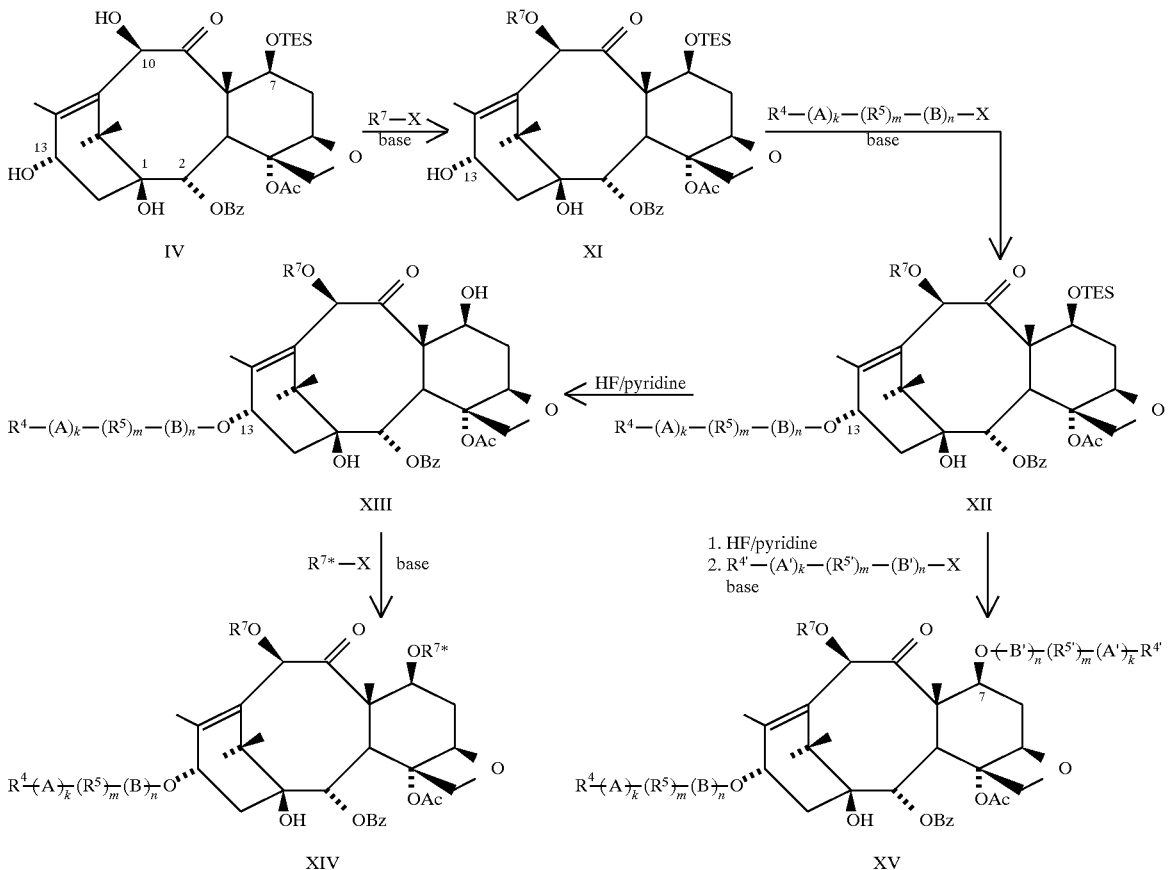

As Scheme 2 above illustrates, 7-TES-10-deacetylbaccatin III(IV) is readily modified at C-10 by reacting with $R^7$—X in the presence of a base to give XI. The compound XI reacts with $R^4$—$(A)_k$—$(R^5)_m$—$(B)_n$—X as defined above to afford XII, which is readily desilylated at C-7 to give XIII. The C-7 desilylation of XII followed by modification with $R^{4'}$—$(A')_k$—$(R^{5'})_m$—$(B')_n$—X at the C-7 defined above, but $R^{4'}$—$(A')_k$—$(R^{5'})_m$—$(B')_n$ moiety is not necessarily the same as $R^4$—$(A)_k$—$(R^5)_m$—$(B)_n$ in this molecule. The desilylated C-7 position of compound XIII can be easily modified with $R^{7*}$—X to give XIV. $R^{7*}$ is selected from $R^7$ defined above, but $R^{7*}$ is not necessarily the same as $R^7$ in this molecule.

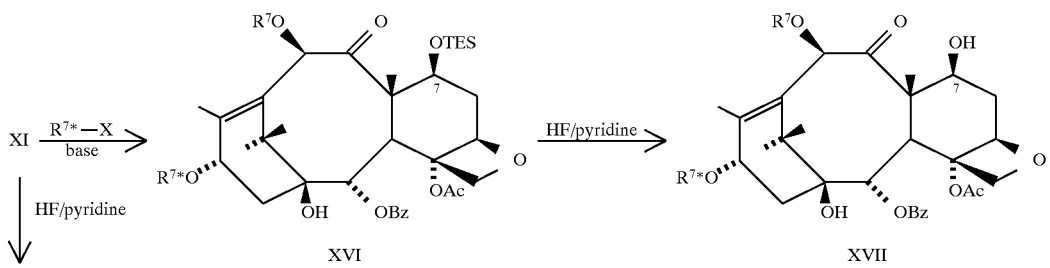

-continued
Scheme 3

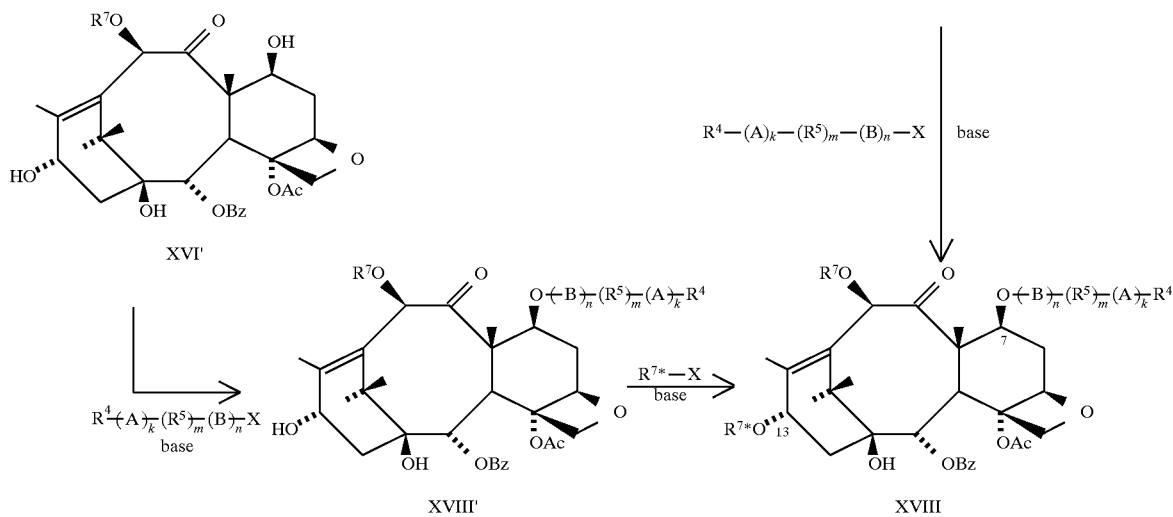

As Scheme 3 above shows, the baccatin derivative XI is deprotected at C-7 to give XVI, which is easily modified at C-13 with $R^{7*}$—X to afford XVII wherein $R^{7*}$—X is as defined above. Then, XVII is readily converted to XVIII through the coupling reaction with $R^4$—$(A)_k$—$(R^5)_m$—$(B)_n$—X. The baccatin derivative XI can also be desilylated at C-7 by HF/pyridine to give XVI', which reacts with $R^4$—$(A)_k$—$(R^5)_m$—$(B)_n$—X to afford XVIII'. This taxoid XVIII' is derived to XVIII with modification at C-13 with $R^{7*}$—X.

Scheme 4

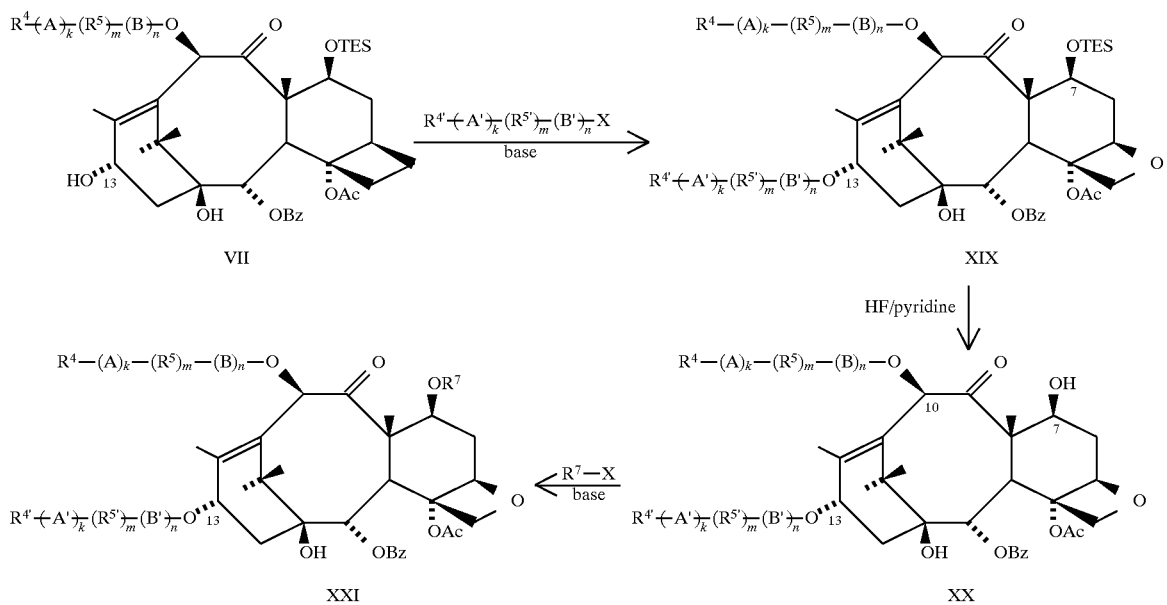

As Scheme 4 above shows, the C-13 position of VII is easily modified with $R^{4'}$—$(A')_k$—$(R^{5'})_m$—$(B')_n$—X wherein $R^{4'}$, $R^{5'}$, A', and B' are as defined above to give XIX. Desilylation of XIX affords XX which has two hydrophobic tethers at C-10 and C-13. Modification of the C-7 position of XX with $R^7$—X yields XXI.

Scheme 5

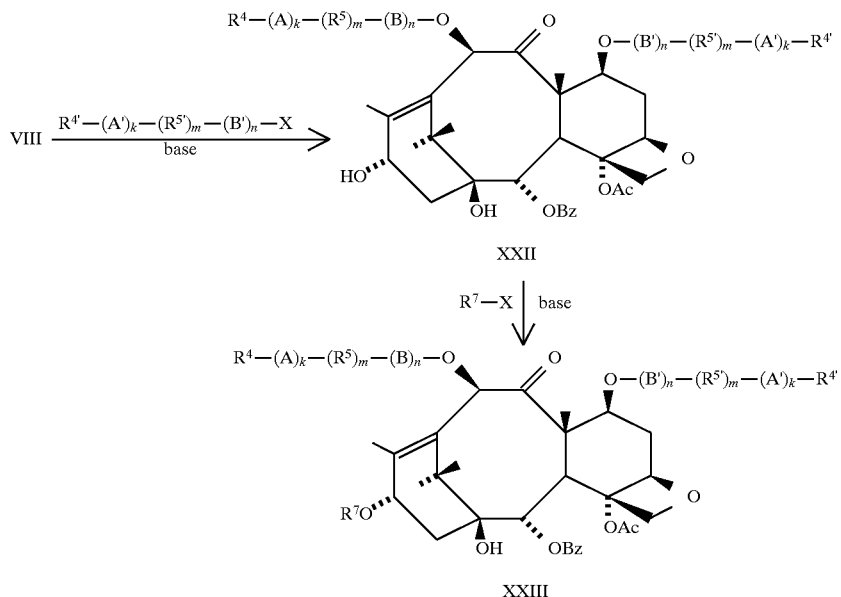

As Scheme 5 above illustrates, the C-7 position of VII can be selectively modified with $R^{4'}$—$(A')_k$—$(R^{5'})_m$—$(B')_n$—X to give XXII. Further modification of the C-13 position of XXII with $R^7$—X affords XXIII.

Scheme 6

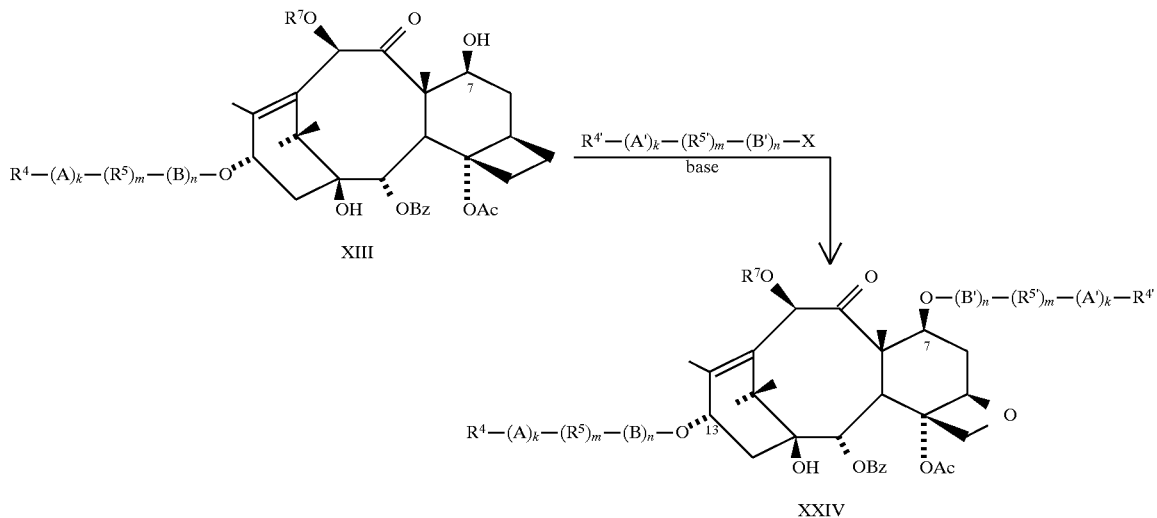

As Scheme 6 above shows, the C-7 position of XIII is readily modified with $R^{4'}$—$(A')_k$—$(R^{5'})_m$—$(B')_n$—X in the presence of a base to give XXIV which has two hydrophobic tethers at C-7 and C-13.

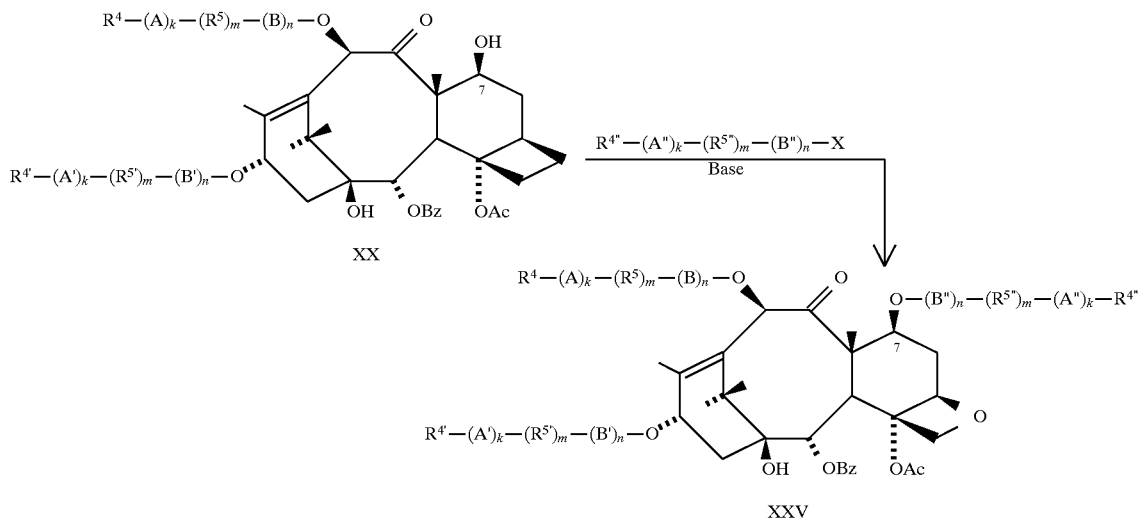
Scheme 7
As Scheme 7 above indicates, the C-7 position of XX can easily be modified with $R^{4''}-(A'')_n-(R^{5''})_m-(B'')_n-X$ to give XXV which has three hydrophobic tethers at C-7, C-10, and C-13. $R^{4''}$, $R^{5''}$, A'', and B'' are selected from $R^4$, $R^5$, A, and B defined above, but $R^4-(A)_k-(R^5)_m-(B)_n$, $R^{4'}-(A')_k-(R^{5'})_m-(B')_n$, and $R^{4''}-(A'')_n-(R^{5''})_m-(B'')_n$ are not necessarily the same group in this molecule.
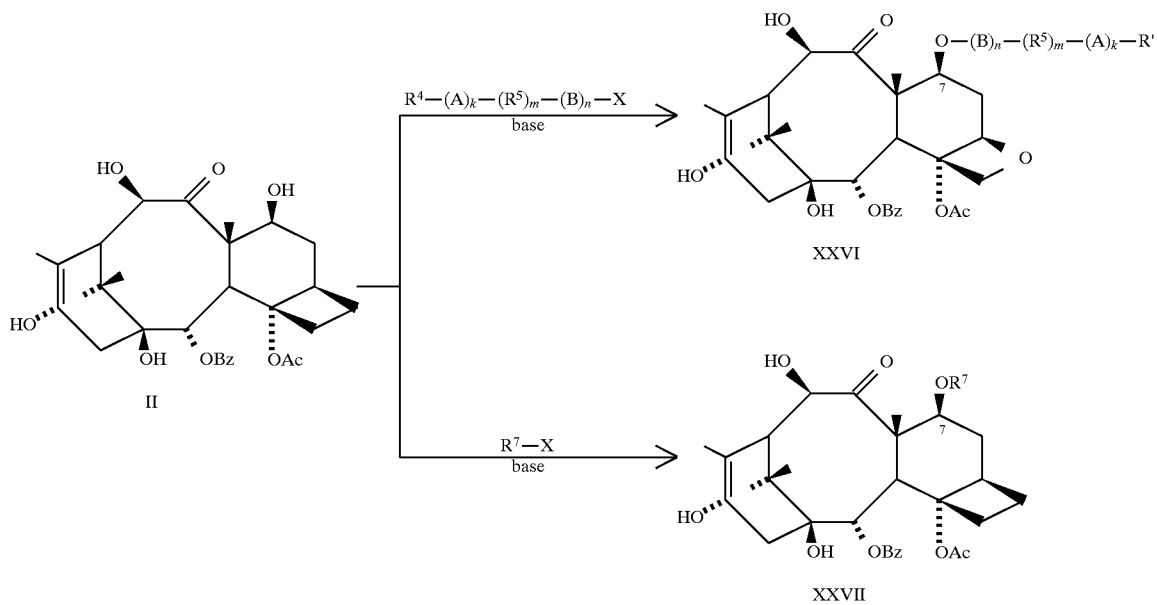
Scheme 8

For the syntheses of taxoid I bearing $R^4$—$(A)_k$—$(R^5)_m$—$(B)_n$ or $R^7$ at C-7, the intermediates XXVI and XXVII can be prepared by directly modifying the C-7 hydroxyl group of 10-deacetylbaccatin III (II) with $R^4$—$(A)_k$—$(R^5)_m$—$(B)_n$—X or $R^7$—X in the presence of a base as shown in Scheme 8 above, wherein the base can be DMAP, LiHMDS and LDA. Further modifications at C-10 and C-13 of compounds XXVI and XXVII can be carried out in the same manner as those shown in Schemes 1–7 shown above.

37, 1408–1410, 1994 which are incorporated herein by reference as if set forth in full. troc-Cl refers to 2,2,2-trichloroethoxylcarbonyl. As usual, the base can be pyridine, triethylamine, or imidazole.

The protected baccatins, XXVIII and XXIX, are further reacted with phosgene in toluene or chloroformates such as

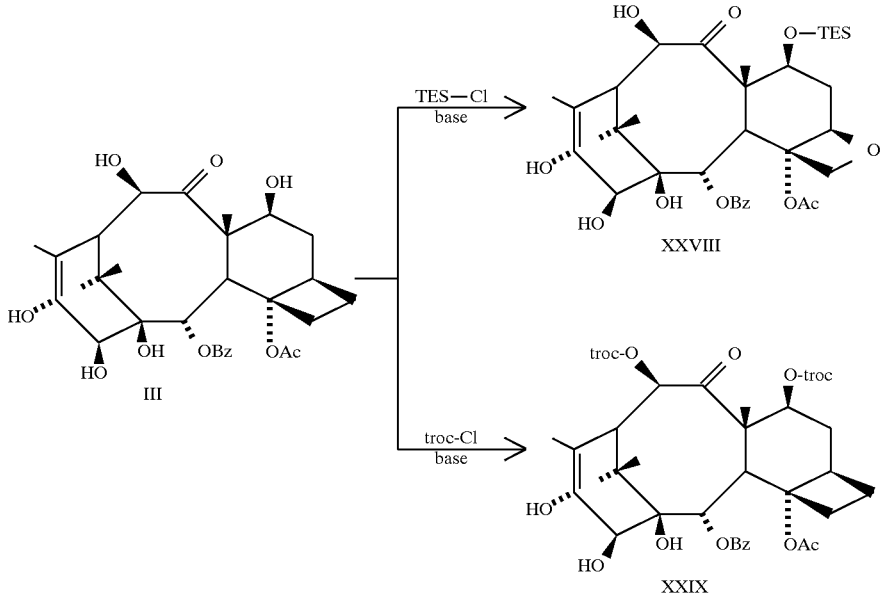

Scheme 9 above shows that 14β-hydroxyl-10-deacetylbaccatin III (III) is readily derivatized to key synthetic intermediates by the reaction with hydroxyl protecting groups such as triethylsilyl (TES) and 2,2,2-trichloroethoxycarbonyl chloride (troc-Cl) to give XXVIII and XXIX, following the literature procedure described by Kant, J. et al. in, "Synthesis and Antitumor Properties of Novel 14-β-Hydroxytaxol and Related Analogues", Bioorg. Med. Chem Lett. 1994, 1565 1994, and Ojima, I. et al. in "Structure-Activity Relationships of New Taxoids Derived from 14β-hydroxyl-10-deacetylbaccatin III", J. Med. Chem.

methyl chloroformate and troc-Cl in the presence of a base to give baccatin-1,4-carbonates, XXX and XXXI, respectively as shown in Scheme 10 below. Deprotections of the C-7 TES group of XXX with HF/pyridine and troc groups at C-7 and C-10 of XXXI with Zn in acetic acid (AcOH)/methanol afford 14β-hydroxyl-10-deacetylbaccatin-1,14-carbonated (XXXII), respectively, in high yields as shown in Scheme 10.

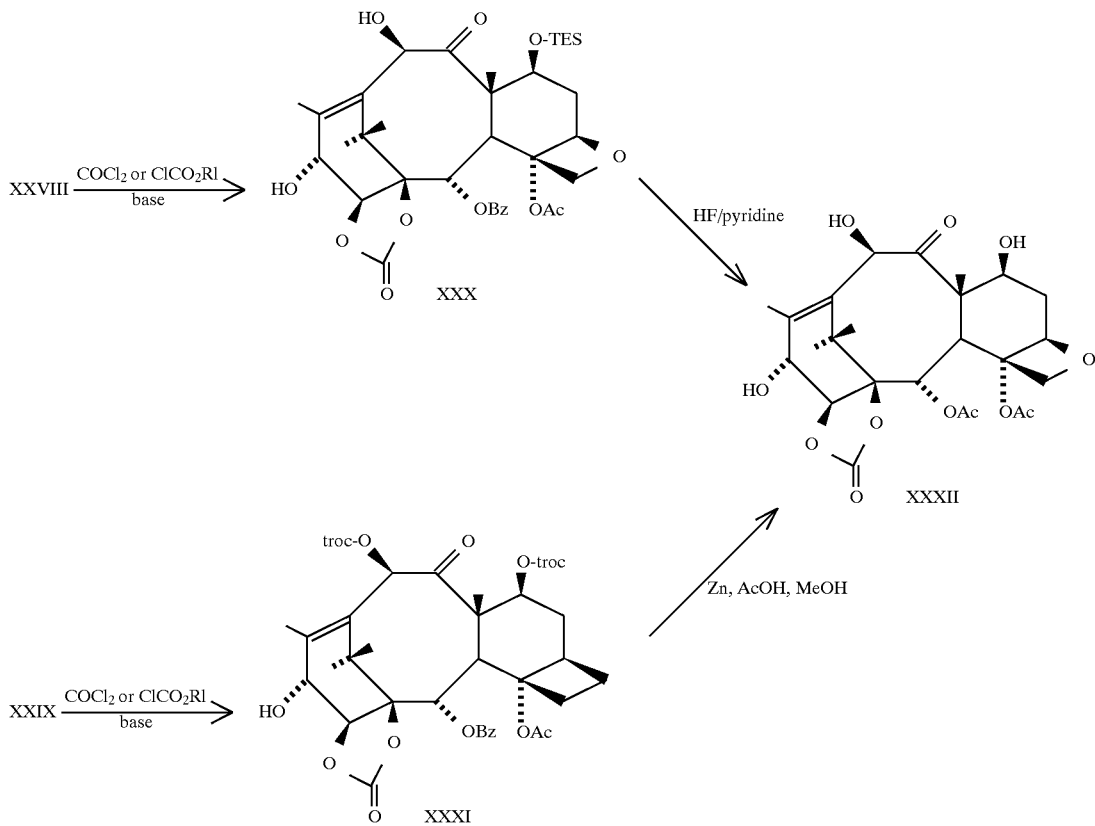

Because of a higher reactivity of the C-14 hydroxyl group in comparison with the sterically hindered C-13 hydroxyl group, the selective modification of XXIX at C-14 is possible using $R^4$—$(A)_k$—$(R5)_m$—$(B)_n$—X or $R^7$—X in the presence of a base, affording XXXIII and XXXIV as shown in Scheme 10 above. The 7,10-ditroc-14-modified baccatins, XXXIII and XXXIV, are readily deprotected by treatment with Zn in acetic acid/methanol to give XXXV and XXXVI, respectively as illustrated in Scheme 11 below.

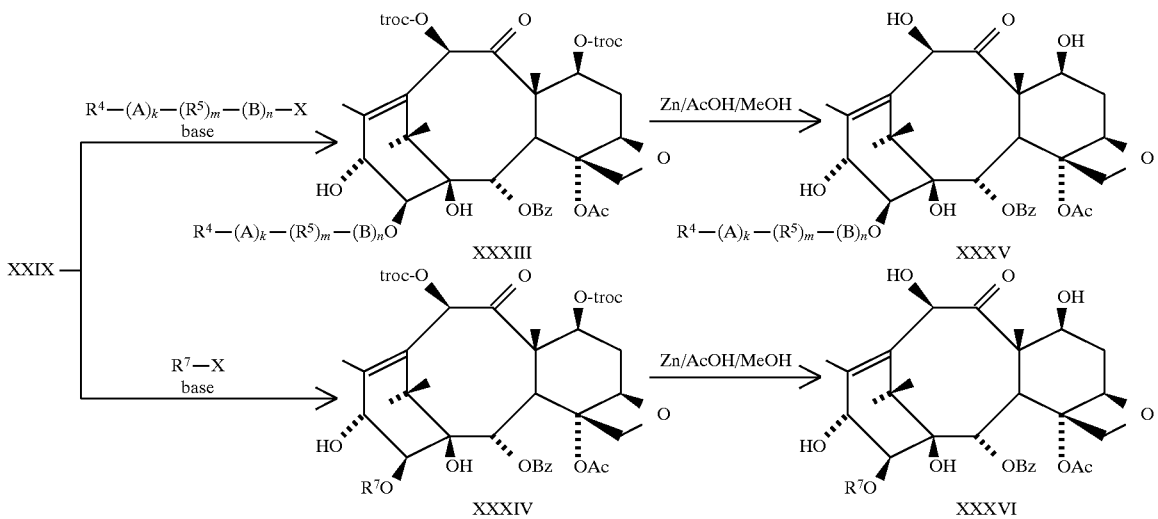

As Scheme 11 shows, the synthetic intermediates XXVIII, XXIX, XXXII, XXXV, and XXXVI, thus obtained, are converted to taxoids I in the same manner as that used for the taxoids I derived from 10-deacetylbaccatin III (II) illustrated in Schemes 1–7. $R^{1'}$ is selected from $R^1$ defined above, but $R^{1'}$ is to necessarily the same as $R^1$ in this molecule. For the cyclic structure at C-1 and C-14 position, 1,14-carbonate is shown as an example. The cyclic structure can also be cyclic sulfonate (X,Y=O—SO2—O), cyclic sulfinate (X,Y=O—SO—O), acetal (X, Y=O—CHR—O), ketal (X, Y=O—CRR'—O) or thiocarbonate (O—C(S)—O), which are easily prepared from vicinal cis-diols.

The hydroxyl protecting group includes methoxylmethyl (MOM), methoxyethyl (MEM), 1-ethyoxyethyl (EE), benzyloxymethyl, (b-trimethylsilylethoxy)methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-trichloroethoxymethyl, trimethylsilyl, triethylsilyl, tripropylsilyl, dimethylethylsilyl, dimethyl(t-butyl)silyl, diethylmethylsilyl, diethylmethylsilyl, dimethylphenylsilyl and diphenylmethylsilyl radical.

The hydroxyl protecting groups can then be removed by using the standard procedures which are generally know to those skilled in the art to give the desired baccatin derivatives. For example, EE and triethylsilyl groups can be removed with 0.5N HCl at room temperature for 12–36 hours, TIPS and TBDMS groups can be removed by treating with fluoride ion in a non-protic organic solvent, and Troc group can be removed with zinc and acetic acid in methanol at 60° C. for 1 hour without disturbing the other functional groups and the skeleton of the taxoids.

The compounds of the invention can be formulated in pharmaceutical preparations or formulated in the form of pharmaceutically acceptable salts thereof, particularly as nontoxic pharmaceutically acceptable acid addition salts or acceptable basic salts. These salts can be prepared from the compounds of the invention according to conventional chemical methods.

Normally, the salts are prepared by reacting free base or acid with stoichiometric amounts or with an excess thereof of the desired salt forming inorganic or organic acid in a suitable solvent or various combination of solvents. As an example, the free base can be dissolved in an aqueous solution of the appropriate acid and the salt recovered by standard techniques, for example, by evaporation of the solution. Alternatively, the free base can be dissolved in an organic solvent such as a lower alkanol, an ether, an alkyl ester, or mixtures thereof, for example, methanol, ethanol, ether, ethyl acetate, an ethyl acetate-ether solution, and the like, whereafter it is treated with the appropriate acid to form the corresponding salt. The salt is recovered by standard recovery techniques, for example, by filtration of the desired salt on spontaneous separation from the solution or it can be precipitated by the addition of a solvent in which the salt is insoluble and recovered therefrom.

Due to their MDR reversing activity, the taxane compounds of the invention can be utilized in the treatment of cancers together with anticancer agents such as paclitaxel, docetaxel, doxorubicin, vinblastine, and vincristine. The new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier, usually about 0.01 mg. up to 2500 mg. or higher per dosage unit, preferably from about 50 to about 500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly (vinylpyrrolidone), calcium carbonate, ethyl oleats, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamne oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The dose administered, whether a single dose, multiple does, or a daily dose, will, of course, vary with the particular compound of the invention employed because of the varying potency of the compound, the chosen route of administration, the size of the recipient and the nature of the patient's condition. The dosage administered is not subject to definite bounds, but it will usually be an effective amount, or the equivalent on a molar basis of the physiologically active free form produced from a dosage formulation upon the metabolic release of the active drug to achieve its desired pharmacological and physiological effects.

The following non-limiting examples are illustrative of the present invention. It should be noted that various changes would be made in the above examples and processes therein without departing from the scope of the present invention. For this reason, it is intended that the illustrative embodiments of the present application should be interpreted as being illustrative and not limiting in any sense.

EXAMPLE 1

Preparation of 7-Triethylsilyl-10-deacetylbaccatin III (IV)

To a stirred solution of 10-deacetylbaccatin III (2 mmol. 1.088 g) in dry pyridine (100 mL) was added dropwise previously distilled chlorotriethylsilane (40 mmol, 6 mL). After stirring the reaction mixture at room temperature for 24 h, pyridine was evaporated under reduced pressure and the crude was purified by column chromatography using ethyl acetate/hexane (1:1) as eluent, affording 1.018 g of 7-TES-10-deacetylbaccatin III (IV) as a white solid (78%).

Identification data for compound IV are shown as follows: $^1$H NMR (300 MHz, CDCl$_3$) δ 0.49 (m, 6H), 0.87 (t, 7.9 Hz, 9H), 1.02 (s, 6H), 1.67 (s, 3H), 1.84 (m, 1H), 2.02 (s, 3H), 2.22 (s, 5H), 2.41 (m, 1H), 3.88 (d, 6.8 Hz, 3H), 4.10 (d, 8.4 Hz, 1H), 4.25 (d, 8.4 Hz, 1H), 4.34 (dd, 10.9 and 6.7 Hz, 1H), 4.81 (m, 1H), 4.89 (dd, 9.5 and 0.9 Hz, 1H), 5.11 (s, 1H), 5.54 (d, 7 Hz, 1H), 7.41 (t, 7.6 Hz, 2H), 7.54 (t, 7.1 Hz, 1H), 8.04 (d, 7.3 Hz, 2H); $^{13}$C NMR (75 MHz, CDCl$_3$) δ 5.16, 6.73, 9.92, 15.13, 19.53, 22.58, 26.63, 37.23, 38.69, 46.99, 67.82, 72.94, 74.66, 74.85, 76.55, 84.27, 128.57, 129.33, 130.05, 133.57, 135.05, 141.81, 167.01, 170.75, 210.33.

EXAMPLE 2

Preparation of 7-triethylsilylbaccatin III (XIa)

To a stirred solution of IV prepared as in Example 1 (200 mg, 0.303 mmol) in dry THF (8 mL) lithium hexamethyldisilazide (LiHMDS) (370 μL, 0.37 mmol) was added dropwise at −40° C. After stirring for 10 min, freshly distilled acetyl chloride (0.703 mmol, 50 μL) was added dropwise and the reaction mixture was stirred for another 40 min at −40° C. The solvent was evaporated under reduced pressure and the crude product was purified by column chromatography on silica gel using ethyl acetate/hexane (1:1) as the eluant, providing 7-TES-bacccatin III (XIa) as a white solid (203 mg, 95% yield). Compound XIa is a specie of compound XI.

Identification data for compound XIa are shown as follows: $^1$H NMR (300 MHz, CDCl$_3$) δ 0.56 (m, 6H), 0.91 (t, 7.9, 9H), 1.02 (s, 3H), 1.17 (s, 3H), 1.66 (s, 3H), 1.85 (m, 1H, 2.15 (s, 6H), 2.27 (s, 5H), 2.51 (m, 1H), 3.86 (d, 7 Hz, 1H), 4.12 (d, 8.2 Hz, 1H), 4.28 (d, 8.2 Hz, 1H), 4.47 (dd, 10.3-6.7 Hz, 1H), 4.81 (m, 1H), 4.93 (d, 9.5 Hz, 1H), 5.61 (d, 7 Hz, 1H), 6.44 (s, 1H), 7.45 (t, 7.6 Hz, 2H), 7.56 (t, 7.1 Hz, 1H), 8.08 (d, 7.3 Hz, 2H); $^{13}$C NMR (63 MHz, CDCl$_3$) δ5.22, 6.71, 9.89, 14.91, 20.04, 20.91, 22.62, 26.74, 37.17, 38.23, 42.72, 47.20, 58.58, 67.83, 72.30, 74.67, 75.75, 76.48, 78.66, 80.76, 84.17, 128.54, 129.33, 130.04, 132.05, 133.57, 144.02, 169.35, 170.67, 202.23.

EXAMPLE 3

Preparation of baccatin III (XVI'a)

To a solution of 7-TES-baccatin III (290 mg, 0.414 mmol) in (1:1) pyridine/acetonitrile (30 mL) 70% hydrogen fluoride in pyridine (2.9 mL) was added dropwise at 0° C. Then the ice bath was removed and the mixture was allowed to stir at room temperature for 4 h. The reaction was quenched with saturated ammonium chloride solution (10 mL). The reaction mixture was extracted with ethyl acetate and the combined organic layers were washed with brine, dried over magnesium sulfate, filtered and concentrated in vacuo. Purification of the crude product by column chromatography on silica gel with ethyl acetate/hexane (2:1) as the eluant gave baccatin III (XVI'a) as a white solid (176 mg, 73% yield).

Identification data for compound XVI'a are shown as follows: $^1$H NMR (300 MHz, CDCl$_3$) δ 0.96 (s, 6H), 1.53 (s, 3H), 1.70 (t, 2.65 Hz, 1H), 1.91 (s, 3H), 2.09 (s, 3H), 2.14 (s, 3H), 2.37 (m, 1H), 3.73 (d, 6.83 Hz, 1H), 4.02 (d, 8 Hz, 1H), 4.15 (d, 8 Hz, 1H), 4.33 (dd, 6.87+10 Hz, 1H), 4.72 (br s, 1H), 4.85 (d, 9.19 Hz, 1H), 5.48 (d, 6.92 Hz, 1H), 6.19 (s, 1H), 7.35 (m, 2H), 7.48 (m, 1H), 7.95 (m, 2H); $^{13}$C NMR (75 MHz, CDCl$_3$) δ 9.42 14.09, 15.41, 20.78, 20.93, 22.38, 26.81, 35.57, 38.94, 42.60, 46.18, 58.48, 60.34, 67.48, 72.15, 74.99, 76.30, 78.84, 80.57, 84.39, 128.54, 129.44, 129,97, 131.34, 133.50, 146.91, 166.79, 170.48, 171.23, 204.24.

EXAMPLE 4

Preparation of 7-triethylsilyl-13-acetylbaccatin III (XVIa)

To a solution of 7-triethylsilyl-10-deacetylbaccatin III (200 mg, 0.3003 mmol) and dimethylaminopyridine (DMAP) (222 mg, 1.82 mmol) in dry dichloromethane (10 mL) acetic anhydride (2.3 mL, 24.4 mmol) was added slowly with stirring. After stirring at room temperature for 2 h, the reaction mixture was treated with a saturated aqueous solution of sodium bicarbonate (10 mL) and stirred for another 20 min. The reaction mixture was then extracted with dichloromethane (3×20 mL). The combined organic layers were washed with brine (25 mL) and dried over magnesium sulfate. The solvent was evaporated and the crude product was purified by column chromatography on silica gel with ethyl acetate/hexane (1:3, then 1:2) as the eluant to give 7-TES-13-Ac-baccatin III (XVIa) as a white solid (184 mg, 82% yield).

Identification data for compound XVIa are shown as follows: $^1$H NMR (300 MHz, CDCl$_3$) δ 0.50 (m, 6H), 0.84 (t, 7.82 Hz, 9H), 1.07 (s, 3H), 1.12 (s, 3H), 1.56 (s, 3H), 1.80 (m, 1H), 1.95 (s, 3H), 2.09 (s, 3H), 2.11 (s, 3H), 2.12 (m, 2H), 2.25 (s, 3H), 2.44 (m, 1H), 3.74 (d, 6.92 Hz, 1H), 4.06 (d, 8.43 Hz, 1H), 4.21 (d, 8.43 Hz, 1H), 4.39 (m, 1H), 4.86 (d, 8.68 Hz, 1H), 5.57 (d, 7 Hz, 2H), 6.05 (t, 8.56 Hz, 1H), 6.37 (s, 1H), 7.38 (t, 7.5 Hz, 2H), 7.51 (t, 7.34 Hz, 1H), 7.98 (d, 7.38 Hz, 2H).

All compounds XVIIa–c are species of compound XVII. They are prepared as described herein.

EXAMPLE 5

Preparation of 13-acetylbaccatin III (XVIIa)

To a solution of 7-TES-13-Ac-baccatin III (184 mg, 0.247 mmol) in a 1:1 mixture of pyridine and acetonitrile (14 mL) a solution of 70% hydrogen fluoride in pyridine (1 mL) with stirring was added dropwise at 0° C. After stirring for 15 h at room temperature, the reaction was quenched with a saturated solution of ammonium chloride (10 mL) and ethyl acetate (10 mL) added. The aqueous layer was extracted with ethyl acetate (3×20 mL), then the combined organic layers were dried over magnesium sulfate and concentrated in vacuo. Purification of the crude product by column chromatography on silica gel with ethyl acetate/hexane (1:1, then 2:1) as the eluant gave 13-acetylbaccatin III (XVIIa) as a white solid (126 mg, 81% yield).

Identification data for XVIIa are set forth as follows: $^1$H NMR (250 MHz, CDCl$_3$) δ 1.08 (s, 3H), 1.18 (s, 3H), 1.62 (s, 3H), 1.86 (m, 4H), 2.16 (s, 3H), 2.19 (s, 3H), 2.22 (m, 2H), 2.28 (s, 3H), 2.5 (m, 2H), 3.78 (d, 6.95 Hz, 1H), 4.12 (d, 8.38 Hz, 1H), 4.25 (d, 8.38 Hz, 1H), 4.38 (m, 1H), 4.92 (d, 7.94 Hz, 2H), 5.61 (d, 7.05 Hz, 1H), 6.13 (t, 8.06 Hz, 1H), 6.26 (s, 1H), 7.38 (t, 7.5 Hz, 2H), 7.51 (t, 7.34 Hz, 1H), 7.98 (d, 7.38 Hz, 2H); $^{13}$C NMR (62.5 MHz, CDCl$_3$) δ 9.40, 14.96, 20.75, 20.92, 22.41, 26.53, 35.50, 35.67, 42.92, 45.74, 58.42, 69.62, 72.01, 74.86, 75.59, 76.26, 78.92, 80.91, 84.27, 93.07, 128.53, 129.14, 129.90, 142.68, 166.71, 169.66, 170.09, 171,10, 203.64.

EXAMPLE 6

Preparation of 7-[N-carbobenzyloxyglycinyl] baccatin III (XVIIb)

To a solution of baccatin III (130 mg, 0.22 mmol), N-Cbz-glycine (69 mg, 0.33 mmol) and DMAP (14 mg, 0.11 mmol) in dry dichloromethane (10 mL) was added dicyclohexyl carbodiimide (DCC) (91 mg, 0.443 mmol) with stirring. After stirring for 3.5 h at room temperature, the white precipitate was filtrated off and the filtrate evaporated in vacuo. The crude product was purified by column chromatography on silica gel with ethyl acetate/hexane (1:1) as the eluant, giving 7-(N-Cbz-Gly)baccatin III (XVIIb) as a white solid (149 mg, 86% yield).

Identification data for XVIIb are set forth as follows: $^1$H NMR (250 MHz, CDCl$_3$) δ 1.09 (s, 3H), 1.15 (s, 3H), 1.75 (s, 3H), 1.85 (m, 1H), 2.05 (s, 3H), 2.18 (s, 3H), 2.25 (s, 5H), 2.55 (m, 1H), 2.7 (d, 1H, OH), 3.8 (dd, 1H), 3.9–4.35 (m, 4 H), 4.85 (m, 1H), 4.95 (d, 1H), 5.1 (dd, 2H), 5.5 (m, 1H), 5.6 (d, 1H), 5.7 (dd, 1H), 6.15 (s, 1H), 7.28 (m, 5H), 7.42 (t, 2H), 7.55 (t, 1H), 8.1 (d, 2H); $^{13}$C NMR (60 MHz, CDCl$_3$) δ

10.59, 15.21, 20.04, 20.86, 22.43, 24.86, 25.51, 26.53, 33.14, 33.82, 38.50, 42.66, 43.00, 47.36, 49.05, 56.08, 66.87, 67.59, 72.16, 74.22, 76.22, 78.48, 80.40, 83.82, 128.00, 128.02, 128.40, 128.56, 129.21, 129.99, 130.93, 133.61, 136.38, 145.29, 156.70, 166.82, 169.49, 169.76, 170.54, 202.28.

EXAMPLE 7

Preparation of 7-triethylsilyl-10-[N-carbobenzyloxyglycinyl]-10-deacetylbaccatin III (XVIIc)

To a solution of 7-TES-10-deacetylbaccatin III (20 mg, 0.030 mmol) in dry tetrahydrofuran THF (1 ML) LiHMDS was added dropwise (0.08 mmol, 80 μL) at −40° C. After stirring for 5 min, a solution of N-Cbz-glycinyloxysuccinimide (0.036 mmol), 11 mg) in dry THF (1 mL) was added at −40° C. The reaction mixture was stirred for 1 h with the temperature allowed to raise to 0° C., then quenched with a saturated solution of ammonium chloride (10 mL). The aqueous layer was extracted with ethyl acetate (3×15 mL) and the combined organic layers were concentrated in vacuo. The crude product was purified by column chromatography on silica gel with ethyl acetate/hexane (1.2, then 1:1) as the eluant, giving XVIIc as a white solid (14 mg, 77% conversion yield).

Identification data for XVIIc are listed as follows: $^1$H NMR (CDCl$_3$, 250 MHz) δ 0.58 (q, 6H), 0.91 (t, 9H), 1.0 (s, 3H), 1.13 (s, 3H), 1.26 (m, 1H), 1.66 (s, 3H), 1.86 (m, 1H), 2.15 (s, 3H), 2.26 (br s, 5H), 2.52 (m, 1H), 3.85 (d, 6.96 Hz, 1H), 4.12 (m, 3H), 4.28 (t, 8.28 Hz, 1H), 4.47 (m, 1H), 4.80 (m, 1H), 4.94 l(d, 8.27 Hz, 1H), 5.10 (s, 2H), 5.37 (m, 1H), 5.60 (d, 6.94 Hz, 1H), 6.49 (s, 1H), 7.33 (m, 5H), 7.45 (t, 2H), 7.58 (t, 1H), 8.08 (d, 2H); $^{13}$C NMR (CDCl$_3$, 62.5 MHz) δ 5.31, 6.77, 9.94, 15.03, 20.11, 22.64, 26.68, 37.20, 38.34, 42.67, 42.87, 47.23, 58.70, 67.14, 67.84, 72.39, 74.66, 76.59, 78.68, 68.80, 80.77, 84.16, 128.11, 128.15, 128.20, 128.53, 128.60, 129.37, 130.08, 132.06; 133.63, 136.13, 144.78, 156.70, 167.05, 168.37, 170.72, 201.93.

Compounds XVIII'a–d are species of compound XVIII'. They are prepared as described hereinbelow.

EXAMPLE 8

Synthesis of 7-[3-(2-naphthyl)-2-propenoyl]baccatin III (XVIII'a) (SB-RA-30011)

To a stirred solution of dry benzene (5 mL) 3-(2-naphthyl)-2-propenoic acid (0.746 mmol, 148 mg) and thionyl chloride (440 mg, 3.671 mmol) were added. After refluxing the mixture for 2.5 h, the solvent was evaporated in vacuo to give a yellowish solid. The solid was dissolved in 3 mL dry dichloromethane and slowly added to a stirred solution of 7-TES-baccatin III (96 mg, 0.163 mmol), 4-dimethylaminopyridine (DMAP) (0.163 mmol, 20 mg) and triethylamine (84 mg, 0.817 mmol) in dry methylene chloride (3 mL). After stirring for 19 h, the reaction mixture was washed with brine (10 mL), saturated sodium bicarbonate (2×15 mL) and brine again (2×15 mL). The organic phase was dried over magnesium sulfate, filtered and concentrated in vacuo. Purification of the crude product by column chromatography on silica gel using ethyl acetate/hexane (1:1) as the eluant were gave XVIII'a as a slightly yellow solid (68 mg, 54% yield).

Identification data for compound XVIII'a are shown as follows: mp 184°–186° C., $[α]_D^{22}$ −64.8° (c 0.54, CH$_2$Cl$_2$); IR (KBr disk) 3489, 2945, 1719, 1635, 1438, 1371, 1236, 1164, 1109, 1069, 1018, 979, 912, 851, 816, 710 cm$^{-1}$; $^1$H NMR (300 MHz, CDCl$_3$) δ 1.02 (s, 3H), 1.10 (s, 3H), 1.85 (s, 4H), 2 (s, 3H), 2.10 (s, 3H), 2.25 (s, 5H), 2.68 (m, 1H), 4.02 (d, 6.78 Hz, 1H), 4.13 (d, 8.3 Hz, 1H), 4.29 (d, 8.3 Hz, 1H), 4.81 (m, 1H), 4.97 (d, 8.9 Hz, 1H), 5.62 (d, 6.93 Hz, 1H), 5.69 (dd, 7.39+10.13 Hz, 1H), 6.35 (s, 1H), 6.40 (d, 16 Hz, 1H), 7.39–7.88 (m, 11H), 8.06 (d, 7.38 Hz, 2H); $^{13}$C NMR (75 MHz, CDCl$_3$) δ 10.87, 15.15, 20.16, 20.62, 22.53, 26.62, 33.48, 38.63, 42.80, 47.41, 56.37, 67.82, 71.95, 74.51, 75.73, 76.37, 78.63, 80.68, 84.09, 118.34, 123.87, 126.54, 127.05, 127.70, 128.45, 128.54, 128.60, 129.37, 129.86, 130.06, 131.73, 132.14, 133.27, 133.62, 134.16, 144.80, 165.82, 166.94, 168.62, 170.64, 202.70. Anal. Calcd. for C$_{44}$H$_{46}$O$_{12}$: C, 68.92; H, 6.05. Found: C, 69.09; H, 6.25.

EXAMPLE 9

7-[3-(2-Naphthyl)propanoyl]baccatin III (XVIII'b) (SB-RA-30021)

3(2-naphtyl)propanoic acid 2 (116 mg, 0.583 mmol) and thionyl chloride (340 mg, 2.86 mmol) were added to a stirred solution of dry benzene (5 mL). After refluxing the mixture for 2.5 h, the solvent was evaporated in vacuo to give a yellowish solid. The solid was dissolved in 3 mL dry methylene chloride and slowly added to a stirred solution of baccatin III (120 mg, 0.204 mmol), DMAP (25 mg, 0.204 mmol) and triethylamine (82 mg, 0.816 mmol) in dry methylene chloride (3 mL). After stirring for 14 h, the reaction mixture was washed with brine (10 mL), saturated sodium bicarbonate (10 mL) and brine again (2×10 mL). The organic layer was dried over magnesium sulfate, filtered and concentrated in vacuo. Purification of the crude product by column chromatography on silica gel with ethyl acetate/hexane (1:1) as the eluant gave XVIII'b as a white solid (104 mg, 66% yield).

Identification data for XVIII'b are set forth as follows: mp 222°–223° C., $[α]_D^{22}$ −77° (c 0.87, CH$_2$Cl$_2$); IR (KBr disk) 3419, 2950, 1718, 1375, 1243, 1066 cm$^{-1}$, $^1$H NMR (300 MHz, CDCl$_3$) δ 1.01 (s, 3H), 1.07 (s, 3H), 1.67 (m, 1H), 1.72 (s, 3H), 2.05 (s, 3H), 2.13 (s, 3H), 2.22 (s, 5H), 2.45 (m, 1H), 2.63 (m, 1H), 2.72 (m, 1H), 3.02 (m, 2H), 3.81 (d, 6.89 Hz, 1H), 4.02 (d, 8.3 Hz, 1H), 4.24 (d, 8.3 Hz, 1H), 4.78 (t, 8.21 Hz, 1H), 4.87 (d, 8.39 Hz, 1H), 5.58 (m, 2H), 6.25 (s, 1H), 7.23–7.73 (m, 10H), 8.04 (d, 7.4 Hz, 2H); $^{13}$C NMR (75 MHz, CDCl$_3$) δ 10.76, 14.18, 15.21, 20.15, 20.83, 21, 22.53, 26.66, 30.62, 33.33, 35.57, 38.61, 42.82, 47.44, 56.22, 60.40, 67.85, 71.65, 74.47, 75.92, 76.33, 78.63, 80.68, 83.99, 125.21, 125.89, 126.35, 127.15, 127.46, 127.58, 127.91, 128.63, 129.37, 130.09, 131.62, 132.12, 133.65, 138.39, 144.79, 166.96, 169, 170.64, 172.12, 202.43. Anal. Calcd. for C$_{44}$H$_{48}$O$_{12}$: C, 68.57; H, 6.40. Found: C, 68.74; H, 6.29.

EXAMPLE 10

7-[4-Benzoylcinnamoyl]baccatin III (XVIII'c) (SB-RA-31011)

To a stirring solution of baccatin III (37 mg, 0.063 mmol) and DMAP (46 mg, 0.378 mmol) in dry dichloromethane (3 mL) a solution of 4-benzoylcinnamyl chloride (48 mg, 0.189 mmol) in dry dichloromethane (2 mL) was slowly added. After stirring for 3 h, the reaction was quenched with a saturated solution of ammonium chloride (10 mL) and extracted with dichloromethane (3×15 mL). The organic layer was washed with a saturated solution of sodium bicarbonate (10 mL) and dried over magnesium sulfate, filtered and concentrated in vacuo. Purification of the crude product by column chromatography on silica gel with ethyl acetate/hexane (1:3, then 1:1) as the eluant gave XVIII'c as a white solid (25 mg, 50% yield).

Identification data for XVIII'c are given as follows: mp 165°–168° C. $[\alpha]_D^{20}$ –70.6° (c 0.016, $CH_2Cl_2$); IR (KBr disk) 3518, 3068, 2968, 1723, 1652, 1601, 1371, 1314, 1238, 1162, 1069, 1019, 983, 707 $cm^{-1}$; $^1H$ NMR (250 MHz, $CDCl_3$) δ 1.07 (s, 3H), 1.14 (s, 3H), 1.71 (m, 1H), 1.87 (s, 3H), 2.07 (s, 3H), 2.14 (s, 3H), 2.29 (m, 5H), 2.71 (m, 1H), 4.04 (d, 6.86 Hz, 1H), 4.17 (d, 8.3 Hz, 1H), 4.33 (d, 8.3 Hz, 1H), 4.86 (m, 1H), 5.00 (d, 8.81 Hz, 1H), 5.70 (m, 2H), 6.36 (s, 1H), 6.44 (d, 16 Hz, 1H), 7.45–7.81 (m, 13H), 8.10 (d, 7.33 Hz, 2H); $^{13}C$ NMR (60 MHz, $CDCl_3$) δ 10.83, 15.19, 20.12, 20.67, 22.54, 26.61, 33.41, 38.50, 42.77, 44.32, 47.37, 56.29, 67.84, 72.16, 74.39, 75.70, 76.34, 78.62, 80.61, 83.98, 120.64, 127.99, 128.35, 128.62, 129.28, 129.96, 130.07, 130.45, 131.68, 132.58, 133.68, 137.34, 138.46, 143.20, 144.79, 165.38, 166.96, 168.70, 170.67, 196.55, 202.63. Anal. Calcd. for $C_{47}H_{48}O_{13}$; C, 68.77; H, 5.89. Found: C, 68.54; H, 5.84.

EXAMPLE 11

7-[3-(4-Benzoylphenyl)propanoyl]baccatin III (XVIII'd) (SB-RA-31021)

A solution of 3-(4-benzoylphenyl)propanoic acid (60 mg, 0.234 mmol) in neat thionyl chloride was stirred for 16 hours. Thereafter, thionyl chloride was evaporated on a rotary evaporator and the resulting yellow oil was dried under vacuum for 1 hour. The residual oil was dissolved in dry dichloromethane (1.5 mL) and slowly added to the stirred solution of baccatin III (80 mg, 0.136 mmol) and DMAP (20 mg, 0.164 mmol) in dry dichloromethane (1.5 mL). After stirring for 21 hours, the reaction was quenched with a saturated solution of ammonium chloride (10 mL) and extracted with dichloromethane (3×15 mL). The organic layer was washed with brine (20 mL) and dried over magnesium sulfate, filtered and concentrated in vacuo. Purification of the crude product by column chromatography on silica gel with ethyl acetate/hexane (1:1) then (3:2) as the eluant gave XVIII'd (86 mg, 79% yield) as a white solid.

Identification data for compound XVIII'd are provided as follows: $^1H$ NMR (250 MHz, $CDCl_3$) δ 1.05 (s, 3H), 1.11 (s, 3H), 1.71 (m, 1H), 1.76 (s, 3H), 2.08 (s, 3H), 2.16 (s, 3H), 2.26 (m, 5H), 2.5–2.73 (m, 3H), 2.99 (m, 2H), 3.97 (d, 6.78 Hz, 1H), 4.12 (d, 8.3 Hz, 1H), 4.28 (d, 8.3 Hz, 1H), 4.84 (t, 7.66 Hz, 1H), 4.93 (d, 8.73 Hz, 1H), 5.61 (m, 2H), 6.26 (s, 1H), 7.3 (d, 8.11 Hz, 2H), 7.44 (m, 4H), 7.55 (m, 2H), 7.72 (m, 4H), 8.04 (d, 7.2 Hz, 2H); $^{13}C$ NMR (62.5 MHz, $CDCl_3$) δ 10.67, 15.17, 20.06, 20.81, 22.45, 26.54, 30.36, 33.25, 35.11, 38.52, 42.7, 47.34, 56.05, 67.66, 71.7, 74.31, 75.84, 76.23, 78.5, 80.48, 83.84, 128.16, 128.25, 128.56, 129.24, 129.88, 130, 130.31, 131.31, 132.18, 133.6, 135.37, 137.73, 144.94, 146.05, 166.84, 169.03, 170.59, 171.72, 196.55, 202.39.

EXAMPLE 12

7-(2-Benzoylcinnamoyl)-13-acetylbaccatin III (XVIIIa) (SB-RA-31012)

To a stirring solution of 13-acetylbaccatin III (50 mg, 0.079 mmol) and DMAP (58 mg, 0.477 mmol) in dry dichloromethane (3 mL) a solution of 4-benzoylcinnamyl chloride (60 mg, 0.238 mmol) in dry dichloromethane (2 mL) was slowly added. After stirring for 6.5 hours, the reaction mixture was quenched with a saturated solution of ammonium chloride (10 mL) and extracted with dichloromethane (3×15 mL). The organic layer was washed with a saturated solution of sodium bicarbonate (20 mL) and dried over magnesium sulfate, filtered and concentrated in vacuo. Purification of the crude product by column chromatography on silic gel with ethyl acetate/hexane (1:3, then 1:1) as the eluant gave XVIIIa as a white solid (26 mg, 38% yield).

Identification data for compound XVIIIa are set forth as follows: mp 158°–161° C. $[\alpha]_D^{20}$ –57.6° (c 1.7, $CH_2Cl_2$); IR (KBr disk) 3491, 3021, 2949, 1724, 1659, 1603, 1449, 1372, 1273, 1239, 1161, 1069, 1019, 983, 708 $cm^{-1}$; $^1H$ NMR (250 MHz, $CDCl_3$) δ 1.17 (s, 3H), 1.20 (s, 3H), 1.67 (s, 1H), 1.87 (s, 3H), 2.00 (m, 4H), 2.07 (s, 3H), 2.20 (s+m, 5H), 2.35 (s, 3H), 2.71 (m, 1H), 4.00 (d, 6.58 Hz, 1H), 4.18 (d, 8.35 Hz, 1H), 4.33 (d, 8.35 Hz, 1H), 4.99 (d, 9.67 Hz, 1H), 5.70 (m, 2H), 6.17 (t, 7.8 Hz, 1H), 6.36 (s, 1H), 6.44 (d, 16 Hz, 1H), 7.45–7.81 (m, 13H), 8.10 (d, 7.33 Hz, 2H); $^{13}C$ NMR (62.5 MHz, $CDCl_3$) δ 10.89, 14.77, 20.63, 20.71, 21.23, 22.47, 26.35, 33.4, 35.57, 43.11, 47.14, 56.21, 69.54, 71.95, 74.46, 75.21, 76.32, 78.80, 80.84, 83.94, 120.58, 128, 128.35, 128.67, 129.15, 129.97, 130.05, 130.46, 132.57, 133.78, 137.37, 138.4, 138.52, 141.48, 143.29, 165.33, 166.95, 168.65, 169.57, 170.21, 195.95, 202.28. Anal. Calcd, for $C_{49}H_{50}O_{14}$: C, 68.20,H, 5.84. Found C, 68.18,H, 5.88.

EXAMPLE 13

7-[3-(2-Naphtyl)propanoyl]-13-acetylbaccatin III (XVIIIb) (SB-RA-30012)

A solution of 3-(2-naphtyl)propanoyl chloride (0.334 mmol, 66 mg) in dry dichloromethane (2 mL) was slowly added to a solution of 13-acetylbaccatin III (70 mg, 0.111 mmol) and DMAP (81 mg, 0.668 mmol) in dry dichloromethane (3 mL). After stirring for 2 hours, the reaction was quenched with a saturated solution of ammonium chloride (10 mL) and extracted with dichloromethane (3×15 mL). The organic layer was washed with a saturated solution of sodium bicarbonate (20 mL) and dried over magnesium sulfate, filtered and concentrated in vacuo. Purification of the crude product by column chromatography on silica gel with ethyl acetate/hexane (1:3, then 1:1) as the eluant, followed by recrystallization in ethyl acetate/hexane gave XVIIIb as a white solid (49 mg, 54% yield).

Identification data for XVIIIb are provided as follows: mp 181°–184° C.; $[\alpha]_D^{20}$ –56.25° (c 0.16, $CH_2Cl_2$); IR (KBr disk) 3460, 2954, 1747, 1722, 1633, 1436, 1371, 1314, 1236, 1149, 1065, 1022, 980, 713 $cm^{-1}$; $^1H$ NMR (250 MHz, $CDCl_3$) δ 1.20 (s, 6H), 1.69 (s, 1H), 1.90 (s, 3H), 1.97 (m, 1H), 2.02 (s, 3H), 2.05 (s, 3H), 2.24 (m, 5H), 2.35 (s, 3H), 2.73 (m, 1H), 4.02 (d, 7 Hz, 1H), 4.19 (d, 8.06 Hz, 1H), 4.34 (d, 8.06 Hz, 1H), 5.01 (d, 8.62 Hz, 1H), 5.72 (m, 2H), 6.17 (t, 8.25 Hz, 1H), 6.40 (s, 1H), 6.46 (d, 16 Hz, 1H), 7.45–7.93 (m, 11H), 8.09 (d, 7.59 Hz, 2H); $^{13}C$ NMR (60 MHz, $CDCl_3$) δ 10.91, 14.77, 20.59, 20.70, 21.23, 22.47, 26.35, 33.44, 35.55, 43.10, 47.13, 56.26, 69.55, 71.69, 74.51, 75.18, 76.33, 78.82, 80.85, 84, 87.21, 118.3, 123.87, 126.55, 127.07, 127.71, 128.46, 128.55, 128.65, 129.17, 129.92, 130.04, 132.13, 132.62, 133.25, 134.16, 141.44, 144.83, 165.73, 166.94, 168.55, 169.49, 170.22, 202.36. Anal. Calcd. for $C_{46}H_{48}O_{13}$; C, 68.13; H, 5.98. Found: C, 68.50; H, 6.09

EXAMPLE 14

10-[(4-Benzoyl)cinnamoyl]-10-deacetylbaccatin III (VIIIa) (SB-RA-4001)

To a solution of 7-TES-10-deacetylbaccatin III (144 mg, 0.218 mmol) in dry THF (5 mL) at –40° C. lithium hexamethyldisilazide (LiHMDS) (260 μL, 0.26 mmol) was added dropwise. After stirring for 5 min, 4-benzoylcinnamoyloxysuccinimide (78 mg, 0.24 mmol) in dry THF (4 mL) was added dropwise at −40° C. and the reaction mixture was stirred for another 30 min. The mixture was then warmed up to room temperature and quenched with 1M ammonium chloride (15 mL). The aqueous phase was extracted with dichloromethane and the organic layer was dried over magnesium sulfate, filtered and concentrated in vacuo. The crude product was purified by column chromatography on silica gel using ethyl acetate/hexane (1:1) as the eluant, giving 106 mg of a white solid. This solid was dissolved in 10 ml pyridine/acetonitrile (1:1) and the solution was cooled down to 0° C. Hydrogen fluoride (70% in pyridine, 1 mL) was added dropwise, then the ice bath was removed and the reaction mixture was allowed to stir at room temperature for 4 h. The reaction was quenched with saturated ammonium chloride solution (5 mL), the solution was extracted with ethyl acetate and the organic layer was washed with brine, dried over magnesium sulfate, filtered and concentrated in vacuo. Purification of the crude product by column chromatography on silica gel with ethyl acetate/hexane (1:1) as the eluant gave VIIIa as a white solid (57 mg, 34% yield).

Identification data for compound VIIIa are shown as follows: mp 250°–252° C.; $[\alpha]_D^{20}$ −68.2° (c 0.44, CHCl$_3$); IR (KBr disk) 3425, 2950, 1721, 1662, 1639, 1560, 1445, 1400, 1317, 1274, 1166, 1110, 1024, 749, 700 cm$^{-1}$; $^1$H NMR (300 MHz, CDCl$_3$-CD$_3$OD) δ 1.03 (s, 3H), 1.07 (s, 3H), 1.58 (s, 3H), 1.77 (m, 1H), 1.98 (s, 3H), 2.19 (s, 5H), 2.45 (m, 1H), 3.81 (d, 6.95 Hz, 1H), 4.37 (d, 6.80 Hz, 1H), 4.40 (d, 6.80 Hz, 1H), 4.74 (t, 7.84 Hz, 1H), 4.91 (d, 8.38 Hz, 1H), 5.53 (d, 7 Hz, 1H), 6.40 (s, 1H), 6.58 (d, 16 Hz, 1H), 7.34–7.73 (m, 13H), 7.99 (d, 7.35 Hz, 2H); $^{13}$C NMR (75 MHz, CDCl$_3$-CD$_3$OD) δ 9.42, 15.32, 20.99, 22.32, 26.86, 35.69, 38.69, 42.61, 46.44, 58.55, 60.43, 67.26, 71.86, 75.00, 76.40, 78.87, 80.72, 84.49, 119.55, 121.55, 128.03, 128.14, 128.34, 128.51, 129.42, 129.93, 130.47, 131.27, 132.71, 133.53, 137.11, 137.88, 138.85, 144.86, 147.26, 166.26, 166.94, 170.76, 196.16, 204.13. Anal. Calcd. for C$_{45}$H$_{46}$O$_{12}$; C, 69.40; H, 5.95. Found: C, 69.25; H, 5.86

Compounds XIVa–c are species of compound XIV. They are prepared as described hereinbelow.

EXAMPLE 15

13-(4-Benzoylcinnamoyl)-7,10-bis(2,2,2-trichloroethoxycarbonyl)baccatin III (XIVa) (SB-RA-1101)

To a magnetically stirred solution of 7,10-ditroc-baccatin III (100 mg, 0.11 mmol), which was readily prepared by the reaction of 10-deacetylbaccatin III (II) with 2,2,2-trichloroethyl chloroformate (troc-Cl) in pyridine, were added DMAP (14 mg, 0.11 mmol), 4-benzoylcimmamic acid (73 mg, 0.22 mmol), and dicyclohexylcarbodiimide (DCC) (454 mg, 2.20 mmol). All three of the latter compounds were added in toluene (10 mL) at room temperature. After 4 hours, TLC analysis showed no starting material. The mixture was concentrated and the dicyclohexylurea (DCU) and excess DCC were removed by passing through a silica gel column using hexane/EtOAc (1/1) as the eluant, which gave crude product. Purification of the crude product by column chromatography on silica gel using hexane/EtOAc (1:1) as the eluant afforded XIVa (105 mg, 83%) as a white solid.

Identification data for compound XIVa are given as follows: mp 179°–181° C. $[\alpha]_D$ −24.3° (c 0.54, CHCl$_3$); IR (CDCl$_3$) 3319, 3248, 2919, 2837, 1768, 1702, 1619, 1578, 1531, 1443, 1378, 1308, 1267, 1243, 1167, 1085, 985, 932, 697 cm$^{-1}$; $^1$H NMR (250 MHz, CDCl$_3$) δ 1.28 (s, 3H), 1.88 (s, 3H), 2.15 (s, 3H), 2.22 (m, 1H), 2.31 (s, 3H), 2.48 (m, 1H), 2.66 (m, 1H), 3.47 (m, 2H), 3.75 (m, 2H), 3.97 (d, J=7.2 Hz, 1H), 4.14 (m, 3H), 4.33 (d, J=8.1 Hz, 1H), 4.55 (d, J=11.8 Hz, 1H), 4.78 (s, 1H), 4.92 (d, J=11.8 Hz, 1H), 5.00 (d, J=8.1 Hz, 1H), 5.60 (m, 1H), 5.70 (d, J=6.5 Hz, 1H), 6.62 (d, J=16.0 Hz, 1H), 6.80 (s, 2H), 6.86 (m, 3H), 7.53 (m, 7H), 7.68 (m, 2H), 7.79 (m, 4H), 7.87 (d, J=7.2 Hz, 1H), 8.06 (d, J=7.5 Hz, 1H), $^{13}$C NMR (63 MHz, CDCl$_3$) δ 9.8, 14.2, 14.4, 15.0, 20.1, 20.3, 21.0, 22.6, 24.8, 25.5, 26.3, 26.5, 33.8, 36.0, 36.5, 36.9, 37.0, 42.7, 46.5, 46.7, 49.3, 53.4, 57.6, 57.7, 60.4, 69.9, 70.2, 71.9, 72.1, 74.6, 75.9, 78.9, 81.0, 84.1, 116.9, 126.3, 126.6, 126.9, 127.1, 127.6, 127.9, 128.3, 128.5, 128.7, 129.2, 130.0, 133.7, 135.5, 135.7, 139.1, 139.2, 146.1, 146.7, 153.3, 153.5, 165.1, 169.5, 172.4, 200.6. Anal. Calcd. for C$_{51}$H$_{50}$C$_{16}$O$_{15}$; C, 54.91; H, 4.52. Found: C, 54.88; H, 4.57.

EXAMPLE 16

13-[3-(2-Naphthyl)prop-2-enoyl]-7,10-bis(2,2,2-trichloroethoxycarbonyl)baccatin III (XIVb)

To a magnetically stirred solution of 7,10-ditroc-baccatin III (100 mg, 0.11 mmol) in dry toluene (10 mL) were added acid 3-(2-naphthyl)prop-2-enoic acid (44 mg, 0.22 mmol), DMAP (14 mg, 0.11 mmol), and DCC (454 mg, 2.20 mmol) at room temperature under N2. After stirring for 4 h, TLC analysis showed no starting material. The solvent was removed on a rotary evaporator and the residue was prepurified using silica gel chromatography with hexane/EtOAc (1:1) as the eluant to remove the excess DCC and DCU. Further purification of the crude product using hexane/EtOAc (3:1) as the eluant afforded XIVb (100 mg, 83%) as a white solid.

Identification data for compound XIVb are listed as follows: mp 171°–173° C.; $[\alpha]_D^{20}$ −63.2° (c 0.19, CHCl$_3$); IR (CDCl$_3$) 3060, 2958, 1760, 1719, 1631, 1449, 1431, 1379, 1249, 1161, 1149, 1108, 1061, 979, 814, 720, 703 cm$^{-1}$; $^1$H NMR (250 MHz, CDCl$_3$) δ 1.22 (s, 3H), 1.73 (s, 1H), 1.89 (s, 3H), 2.19 (s, 3H), 2.09 (m, 1H), 2.26 (m, 1H), 2.33 (s, 3H), 2.51 (dd, J=9.1, 15.5 Hz, 1H), 2.69 (m, 1H), 4.00 (d, J=6.9 Hz, 1H), 4.19 (d, J=8.6 Hz, 1H), 4.33 (d, J=8.6 Hz, 1H), 4.33 (d, J=8.6 Hz, 1H), 4.62 (d, J=11.8 Hz, 1H), 4.79 (s, 2H), 4.94 (d, J=11.8 Hz, 1H), 5.02 (d, J=8.9 Hz, 1H), 5.64 (dd, J=7.3, 10.7 Hz, 1H), 5.72 (d, J=6.9 Hz, 1H), 6.23 (m, 1H), 6.32 (s, 1H), 6.63 (d, J=16.0 Hz, 1H), 7.47 (m, 2H), 7.58 (m, 3H), 7.71 (d, J=8.5 Hz, 1H), 7.89 (m, 3H), 8.05 (m, 4H); $^{13}$C NMR (63 MHz, CDCl$_3$) δ 10.7, 15.4, 20.5, 22.6, 26.4, 33.4, 36.1, 42.9, 47.2, 56.3, 69.9, 74.1, 76.3, 76.6, 77.1, 77.4, 78.8, 79.3, 80.7, 83.6, 94.2, 116.9, 123.1, 127.0, 127.7, 127.8, 128.7, 129.0, 130.0, 130.6, 131.3, 131.8, 133.3, 133.8, 134.5, 143.4, 146.9, 153.3, 165.8, 166.8, 170.0, 200.8. Anal. Calcd. for C$_{48}$H$_{46}$C$_{16}$O$_{15}$; C, 54.31; H, 4.56. Found: C, 54.27; H, 4.61.

EXAMPLE 17

13-[3-(2-Naphthyl)prop-2-enoyl]-10-deacetylbaccatin III (XIVc) (SB-RA-2001)

Activated zinc (0.45 g, 6.80 mmol) dust was added to a solution of XIVb (98 mg, 0.100 mol) in AcOH (1.5 mL) and MeOH (1.5 mL). The zinc dust was activated by washing with 10% HCl followed by rinsing with water until the washings became neutral. The zinc was then washed with ether and dried under vacuum overnight. The mixture was heated at 70° C. for 75 min. The reaction mixture was diluted with 100 mL of ethyl acetate and filtered. The filtrate was washed with aqueous saturated NaHCO3, water, and dried over MgSO4. After evaporation of the solvent, purification of the crude product by column chromatography on silica gel using hexane/EtOAc (1:1) as the eluant afforded XIVc (65 mg, 80%) as a white solid.

Identification data for compound XIVc are listed as follows: mp 189°–192° C.; $[\alpha]^{20}_D$ –32.5° (c 0.40, CHCl$_3$); IR (CDCl$_3$) 3448, 2919, 1702, 1631, 1455, 1443, 1367, 1308, 1267, 1243, 1161, 1108, 1067, 1020, 967 cm$^{-1}$; $^1$H NMR (250 MHz, CDCl$_3$) δ 1.15 (s, 3H), 1.26 (s, 3H), 1.70 (m, 2H), 1.79 (s, 3H), 1.93 (m, 1H), 2.09 (s, 3H), 2.24 (m, 1H), 2.30 (s, 3H), 2.46 (dd, J=9.2, 16.0 Hz, 1H), 2.65 (m, 1H), 4.02 (d, J=7.0 Hz, 1H), 4.26 (m, 3H), 4.99 (d, J=8.3 Hz, 1H), 5.71 (d, J=7.0 Hz, 1H), 6.19 (m, 1H), 6.61 (d, J=16.0 Hz, 1H), 7.51 (m, 4H), 7.70 (d, J=9.2 Hz, 1H), 7.89 (m, 2H), 8.03 (m, 3H); $^{13}$C NMR (63 MHz, CDCl$_3$) δ: 9.8, 15.1, 20.2, 22.6, 26.5, 36.5, 37.1, 42.9, 46.8, 57.7, 70.3, 72.1, 74.7, 76.6, 79.0, 81.0, 84.1, 117.1, 123.1, 126.4, 127.6, 127.8, 128.6, 128.9, 129.2, 130.0, 130.5, 131.4, 133.3, 133.7, 134.4, 135.8, 139.3, 143.9, 146.6, 166.3, 166.9, 211.5. Anal. Calcd. for C$_{42}$H$_{46}$O$_{10}$: C, 70.97; H, 6.52. Found: C, 71.01; H, 6.55.

EXAMPLES 18–23

In a manner similar to the syntheses of modified baccatins (taxoids) described above, taxoids of the type XVIII' and XXII were synthesized in good yields as described below. Compounds XVIII'a–c and XXIIa–c are species of compounds XVIII' and XXII, respectively.

To a stirring solution of 7-TES-baccatin III in THF (0.015M) was added 1.2 equivalents of LiHMDS at –40° C. After the mixture was stirred for 5 min, a solution of the N-hydroxysuccinimide ester of 3-(4-benzoylphenyl) propanoic acid or 3-(2-naphtyl)prop-2-enoic acid in THF (1.2 equiv, 1 mL) was added dropwise at –40° C. with stirring. The mixture was warmed to –20° C. over the preiod of 30 min and then the reaction was quenched with saturated aqueous ammonium chloride. The aqueous layer was extracted with ethyl acetate and the combined organic layers were dried over magnesium sulfate, filtered and concentrated in vacuo. Purification of the crude product by flash chromatography on silica gel (eluant: hexane/EtOAc=1/1) afforded the corresponding 10-acyl-7-TES 10-deacetylbaccatin III as a white solid.

To a stirring solution of 10-acyl-7-TES 10-deacetylbaccatin III (0.011M), thus obtained, in a 1:1 mixture of pyridine and acetonitrile was added HF/pyridine (70/30) (1 mL/16 mg of the substrate) at 0° C. After stirring at room temperature for 16 h, the reaction was quenched with saturated aqueous ammonium chloride and extracted with ethyl acetate. The combined organic layers were washed with saturated aqueous copper sulfate and water, then dried over magnesium sulfate, filtered and concentrated in vacuo. Purification of the crude by flash chromatography on silica gel (eluant: hexane/EtOAc=1/2) afforded the corresponding 10-acyl-10-deacetylbaccatin III as a white solid.

To a stirring solution of 10-acyl-10-deacetylbaccatin III (0.015–0.02M), DMAP (0.2 equiv.) and 3-(2-naphtyl) propanoic acid, 3-(4-benzoylphenyl)propanoic acid or Cbz-glycine (1.2 equiv.) in dichloromethane was added. dicyclohexylcarbodiimide (DCC) (1.5 equiv.) at room temperature. After stirring for 16 hours, 1 equivalent of DCC was added. After 17–25 hours, the solvent was evaporated in vacuo. Purification of the crude by flash chromatography on silica gel (eluant: hexane/EtOAc=1/1) afforded the 10-acyl-7-acyl-10-deacetylbaccatin III as a white solid.

7-(N-Carbobenzoxyglycinyl)baccatin III (XVIII'a)

Identification data for Compound XVIII'a obtained in 82% yield are set forth as follows; $^1$H NMR (250 MHz, CDCl$_3$) δ 1.09 (s, 3H), 1.15 (s, 3H), 1.75 (s, 3H), 1.85 (m, 1H), 2.05 (s, 3H), 2.18 (s, 3H), 2.25 (s, 5H), 2.55 (m, 1H), 2.7 (d, 1H, OH), 3.8 (dd, 1H), 3.9–4.35 (m, 4H), 4.85 (m, 1H), 4.95 (d, 1H), 5.1 (dd, 2H), 5.5 (m, 1H), 5.6 (d, 1H), 5.7 (dd, 1H), 6.15 (s, 1H), 7.28 (m, 5H), 7.42 (t, 2H), 7.55 (t, 1H), 8.1 (d, 2H); $^{13}$C NMR (62.5 MHz, CDCl$_3$) δ 10.59, 15.21, 20.04, 20.86, 22.43, 24.86, 25.51, 26.53, 33.14, 33.82, 38.50, 42.66, 43.00, 47.36, 49.05, 56.08, 66.87, 67.59, 72.16, 74.22, 76.22, 78.48, 80.40, 83.82, 128.00, 128.02, 128.40, 128.56, 129.21, 129.99, 130.93, 133.61, 136.38, 145.29, 156.70, 166.82, 169.49, 169.76, 170.54, 202.28.

7-(Naphthalene-2-carbonyl)baccatin III (XVIII'b) (SB-RA-30001)

Identification data for Compound XVIII'b obtained in 58% yield are as follows: mp 251°–252° C.; $[\alpha]^{20}_D$ –56.25° (c 0.16, CH$_2$Cl$_2$); IR (KBr disk) 3469, 2993, 1728, 1640, 1406, 1286, 1240, 1023, 714 cm$^{-1}$; $^1$H NMR (250 MHz, CDCl$_3$) δ 1.07 (s, 3H), 1.17 (s, 3H), 1.91 (s, 3H), 1.99 (s, 4H), 2.18 (s, 3H), 2.32 (s, 5H), 2.84 (m, 1H), 4.12 (d, 6.9 Hz, 1H), 4.22 (d, 8.3 Hz, 1H), 4.36 (d, 8.3 Hz, 1H), 4.86 (m, 1H), 5.04 (d, 8.7 Hz, 1H), 5.71 (d, 6.9 Hz, 1H), 5.86 (m, 1H), 6.47 (s, 1H), 7.46–7.64 (m, 5H), 7.82–7.98 (m, 4H), 8.12 (d, 2H), 8.48 (s, 1H); $^{13}$C NMR (62.5 MHz, CDCl$_3$) δ 11.01, 15.21, 20.16, 20.45, 22.56, 26.60, 33.45, 38.53, 42.77, 47.24, 56.47, 67.88, 72.45, 74.50, 75.48, 76.39, 78.71, 80.64, 84.03, 125.49, 126.31, 127.55, 127.69, 127.83, 128.02, 128.64, 129.31, 1299.55, 130.10, 131.29, 131.87, 132.43, 133.70, 135.52, 144.79, 165.51, 167.04, 168.42, 170.69, 202.95. Anal. Calcd. for C$_{42}$H$_{44}$O$_{12}$: C, 68.10; H, 5.99. Found: C, 68.27; H, 5.83.

7-(Naphthalene-2-carbonylglycyl)baccatin III (XVIII'c) (SB-RA-3201)

A methanol (0.02M) solution of 7-(N-carbobenzoxyglycinyl)baccatin III (XVIII'a), obtained as described above was subjected to hydrogenolysis in the presence of 10% Pd-C (150 weight %) at ambient temperature and pressure for 4.5 hours. The solution was filtered through a pad of celite to remove the catalyst and concentrated in vacuo to afford a white solid. The resulting solid was dissolved in ethyl acetate (0.02M) and naphthalene-2-carbonyl chloride (1.6 equiv) was added. After vigorous stirring for 10 minutes, a saturated aqueous sodium bicarbonate was added. The mixture was stirred for another 10 minutes, then diluted with ethyl acetate washed with brine, and extracted with ethyl acetate. The combined organic layers were dried over magnesium sulfate, filtered and concentrated in vacuo. Purification of the crude product by flash chromatography on silica gel (eluant: hexane/EtOAc= 1//1 then 1/2) afforded XVIII'c as a white solid (71%).

Identification data for compound XVIII'c are set forth as follows: mp 165°–168° C.; $[\alpha]^{20}_D$ –78° (c 2.18, CH$_2$Cl$_2$); IR (KBr disk) 3428, 2969, 1734, 1656, 1538, 1452, 1379, 1248, 1069, 1020, 980, 718 cm$^{-1}$; $^1$H NMR (250 MHz, CDCl$_3$) δ 1.07 (s, 3H), 1.13 (s, 3H), 1.79 (s, 3H), 1.87 (m, 1H), 2.09 (s, 3H), 2.18 (s, 3H), 2.27 (s, 3H), 2.30 (m, 2H), 2.65 (m, 1H), 4.0 (d, 6.8 Hz, 1H), 4.12 (d, 8.3 Hz, 1H), 4.18–4.40 (m, 2H), 4.84 (m, 1H), 4.96 (d, 8.8 Hz, 1H), 5.61 (d, 6.9 Hz, 1H), 5.72 (m, 1H), 6.23 (s, 1H), 7.10 (t, 5.4 Hz, 1H), 7.43–7.59 (m, 5H), 7.85–7.98 (m, 4H), 8.08 (d, 2H), 8.42 (s, 1H); $^{13}$C NMR (62.5 MHz, CDCl$_3$) δ 10.77, 15.31, 20.12, 21.04, 22.51, 26.62, 33.19, 38.51, 42.06, 42.76, 47.44, 56.26, 67.78, 72.62, 74.23, 76.23 78.55, 80.52, 83.84, 123.75, 126.62, 127.59, 127.73, 128.34, 128.62, 129.0, 129.18, 130.04, 131.09, 131.41, 132.68, 133.70, 134.80, 145.24, 166.94, 167.50, 169.23, 170.29, 170.70, 202.45. Anal. Calcd. for C$_{44}$H$_{47}$NO$_{13}$: C, 66.24; H, 5.94; N, 1.76. Found: C, 66.46; H, 5.84; N, 1.75.

7,10-Bis[3-(2-naphthyl)prop-2-enoyl]-10-deacetylbaccatin III (XXIIa) (SB-RA-4101)

Identification data for compound XXIIa is as follows: mp 176°–179° C.; [α]$^{20}_D$ –50° (c 0.5, CH$_2$Cl$_2$); IR (KBr disk) 3422, 2940, 1718, 1631, 1363, 1256, 1163, 1018, 988, 711 cm$^{-1}$; $^1$H NMR (250 MHz, CDCl$_3$) δ 1.15 (s, 3H), 1.28 (s, 3H), 1.94 (m, 4H), 2.22 (s, 3H), 2.34 (s, 3H), 2.37 (m, 2H), 2.83 (m, 1H), 4.13 (d, 6.8 Hz, 1H), 4.23 (d, 8.34 Hz, 1H), 4.37 (d, 8.34 Hz, 1H), 4.90 (t, 7.73 Hz, 1H), 5.05 (d, 8.86 Hz, 1H), 5.75 (m, 2H), 6.53 (d, 15.8 Hz, 1H), 6.55 (d, 16 Hz, 1H), 6.63 (s, 1H), 7.40–8.2 (m, 21H); $^{13}$C NMR (63 MHz, CDCl$_3$) δ 10.95, 15.25, 20.45, 22.57, 24.91, 25.57, 26.74, 33.48, 33.88, 38.59, 42.83, 47.37, 56.50, 67.88, 72.26, 74.55, 75.82, 76.42, 78.76, 80.70, 84.11, 117.37, 118.41, 123.41, 123.90, 126.49, 127.04, 127.13, 127.64, 127.68, 128.35, 128.44, 128.49, 128.64, 129.34, 129.96, 130.10, 131.69, 131.81, 132.25, 133.10, 133.28, 133.68, 134.13, 136.16, 145.04, 145.22, 145.72, 149.57, 164.89, 165.95, 167.01, 170.72, 202.95. Anal. Calcd. for C$_{55}$H$_{52}$O$_{12}$: C, 72.99; H, 5.79. Found: C, 72.82; H, 5.69.

7,10-Bis[3-(4-benzoylphenyl)prop-2-enoyl]-10-deacetylbaccatin III (XXIIb) (SB-RA-4102)

Identification data for compound XXIIb is set forth as follows: mp 132°–135° C.; [α]$^{20}_D$ –54.7° (c 0.53, CH$_2$Cl$_2$); IR (KBr disk) 3444, 2946, 1738, 1651, 1605, 1372, 1278, 1068, 984, 703 cm$^{-1}$; $^1$H NMR (250 MHz, CDCl$_3$) δ 1.04 (s, 3H), 1.11 (s, 3H), 1.78 (s, 3H), 1.89 (m, 1H), 2.10 (s, 3H), 2.29 (m, 5H), 2.48–3.12 (m, 9H), 3.99 (d, 6.8 Hz, 1H), 4.14 (d, 8.3 Hz, 1H), 4.31 (d, 8.3 Hz, 1H), 4.85 (t, 7.9 Hz, 1H), 4.95 (d, 8.74 Hz, 1H), 5.65 (m, 2H), 6.31 (s, 1H), 7.28–7.77 (m, 22H), 8.10 (d, 7.3 Hz, 2H); $^{13}$C NMR (63 MHz, CDCl$_3$) δ 10.72, 15.25, 20.18, 22.51, 24.89, 25.56, 26.62, 30.39, 30.85, 33.32, 33.88, 35.12, 38.50, 42.72, 7.38, 49.13, 56.17, 67.76, 71.70, 74.31, 76.00, 76.28, 78.58, 80.55, 84.89, 128.18, 128.24, 128.59, 129.90, 130.05, 130.34, 130.45, 131.27, 132.18, 132.30, 133.67, 135.47, 137.65, 137.77, 145.09, 145.29, 146.00, 166.93, 170.64, 170.96, 171.70, 196.37, 196.42, 202.34. Anal. Calcd. for C$_{61}$H$_{60}$O$_{14}$: C, 72.03; H, 5.95. Found: C, 71.88; H, 5.71.

7-[3-(2-Naphthyl)prop-2-enoyl]-10-[3-(4-benzoylphenyl)propanoyl]-10-deacetylbaccatin III (XXIIc) (SB-RA-4302)

Identification data for compound XXIIc is as follows: mp 135°–136° C.; [α]$^{20}_D$ –57.4° (c 1.01, CH$_2$Cl$_2$); IR (KBr disk) 3469, 2928, 1724, 1653, 1604, 1447, 1369, 1276, 1152, 1067, 980, 704 cm$^{-1}$; $^1$H NMR (250 MHz, CDCl$_3$) δ 1.04 (s, 3H), 1.14 (s, 3H), 1.91 (m, 4H), 2.16 (s, 3H), 2.29 (m, 2H), 2.31 (s, 3H), 2.69–2.93 (m, 5H), 4.07 (d, 6.9 Hz, 1H), 4.20 (d, 8.3 Hz, 1H), 4.36 (d, 8.3 Hz, 1H), 4.86 (t, 6.6 Hz, 1H), 5.02 (d, 8.8 Hz, 1H), 5.71 (m, 2H), 6.46 (s, 1H), 6.48 (d, 15.8 Hz, 1H), 7.11 (d, 8.2 Hz, 2H), 7.46–7.94 (m, 18H), 8.12 (d, 7.3 Hz, 2H); $^{13}$C NMR (63 MHz, CDCl$_3$) δ 10.92, 15.21, 20.28, 22.55, 24.91, 25.59, 26.65, 30.78, 33.51, 33.90, 35.04, 38.57, 42.77, 47.37, 49.22, 56.46, 67.89, 71.9, 74.49, 75.80, 78.69, 80.73, 84.08, 118.44, 123.73, 126.62, 127.11, 127.47, 127.74, 128.14, 128.21, 128.26, 128.53, 128.58, 128.65, 129.34, 129.89, 130.11, 130.28, 131.70, 132.19, 132.25, 133.29, 133.70, 134.19, 135.54, 137.77, 144.81, 145.04, 145.44, 165.79, 167.02, 170.25, 170.67, 196.38, 202.78. Anal. Calcd. for C$_{58}$H$_{56}$O$_{13}$: C, 72.49; H, 5.87. Found: C, 72.36; H, 5.90.

EXAMPLES 24–26

7-Triethylsilyl-14-(6-phenyl hexanoyl)-10-deacetylbaccatin III (7-TES-XXXVa)

DCC (2.1 equivalents) was added to a solution of 7-triethylsilyl-14-hydroxy-10-deacetybaccatin III (0.026M), dimethylaminopyridine (0.2 equivalents) and 6-phenylhexanoic acid (1.1 equivalents) in dichloromethane at room temperature. After stirring for 48 h, the solvent was evaporated in vacuo. Purification by radial chromatography using hexane/EtOAc as the eluant afforded 7-TES-XXXva as a white solid (95% yield).

Identification data for compound 7-TES-XXXVa is shown as follows: $^1$H NMR (250 MHz, CDCl$_3$) δ 0.56 (m, 6H), 0.95 (t, 9H), 1.05 (s, 3H), 1.14 (s, 3H), 1.41 (m, 6H), 1.71 (s, 3H), 1.92 (m, 1H), 2.11 (s, 3H), 2.37 (s, 3H), 2.45 (m, 3H), 2.61 (t, 7.5 Hz, 2H), 3.95 (d, 7.1 Hz, 1H), 4.22 (d, 8.34 Hz, 1H), 4.28 (d, 8.34 Hz, 1H), 4.42 (m, 1H), 4.65 (m, 1H), 4.97 (d, 8.5 Hz, 1H), 5.20 (s, 1H), 5.36 (d, 5.3 Hz, 1H), 5.79 (d, 7.2 Hz, 1H), 7.08–7.29 (m, 5H), 7.42–7.53 (m, 3H), 8.05 (d, 2H); $^{13}$C NMR (62.5 MHz, CDCl$_3$) δ 5.16, 6.75, 9.86, 15.06, 20.60, 22.45, 24.83, 26.24, 28.36, 30.77, 34.21, 35.68, 37.21, 42.72, 46.47, 58.21, 72.89, 73.50, 74.50, 75.10, 76.40, 76.61, 77.43, 80.47, 84.16, 125.66, 125.75, 128.27, 128.48, 129.33, 130.12, 133.42, 136.18, 138.72, 142.15, 142.41, 165.76, 171.11, 173.67, 209.74.

14-(6-Phenyl hexanoyl)-10-deacetylbaccatin III (XXXVa)

To a solution of 7-TES-XXXVa (0.009M) in a (1:1) mixture of pyridine and acetonitrile was added HF/pyridine (70:30) (1 mL/8 mg of starting material) at 0° C. After stirring at room temperature for 16 hours, the reaction was quenched with a saturated solution of ammonium chloride and extracted with ethyl acetate. The combined organic layers were washed with a saturated solution of copper sulfate and water, then dried over magnesium sulfate, filtered and concentrated in vacuo. Purification of the crude product by chromatography on silica gel (hexane/EtOAc= 1/2) afforded XXXVa as a white solid (72% yield).

Identification data for compound XXXva is shown as follows: $^1$H NMR (250 MHz, CDCl$_3$) δ 1.05 (s, 3H), 1.14 (m, 5H), 1.43 (m, 4H), 1.75 (s, 3H), 1.84 (m, 1H), 2.08 (s, 3H), 2.34 (m, 2H), 2.37 (s, 3H), 2.45 (m, 2H), 2.56 (m, 1H), 2.75 (s, 1H), 3.20 (br s, 1H), 3.98 (d, 7.1 Hz, 1H), 4.27 (m, 3H), 4.64 (m, 1H), 4.98 (d, 9.1 Hz, 1H), 5.28 (s, 1H), 5.35 (d, 5.3 Hz, 1H), 5.80 (d, 7.2 Hz, 1H), 7.08–7.29 (m, 5H), 7.39–7.56 (m, 3H), 8.04 (d, 2H); $^{13}$C NMR (62.5 MHz, CDCl$_3$) δ 9.69, 14.98, 20.77, 22.44, 24.68, 26.07, 28.34, 30.74, 34.21, 35.39, 36.84, 42.62, 46.36, 57.95, 71.93, 73.47, 74.79, 75.02, 76.42, 76.61, 77.55, 80.55, 84.11, 125.74, 128.27, 128.50, 129.24, 130.10, 133.47, 135.89, 139.06, 142.15, 165.77, 171.08, 173.70, 211.07,

14-(6Phenyl hexanoyl) 7,13-diacetyl baccatin III (7,10-Ac2-XXXVa)

Acetic anhydride (30 equivalents) was added to a solution of XXXVa (0.026M) and DMAP (6 equivalents) in dichloromethane. After stirring at room temperature for 3 h, the reaction was quenched with a saturated solution of ammonium chloride and extracted with dichloromethane. The combined organic layers were dried over magnesium sulfate, filtered and concentrated in vacuo. Purification of the crude by chromatography on silica gel (hexane/EtOAc= 1/3) afforded 7,10-Ac2-XXXVa as a white solid (87% yield).

Identification data for compound 7,10-ALZ XXXVa is set forth as follows: mp 191°–193° C.; $^1$H NMR (250 MHz, CDCl$_3$) δ 1.11 (m, 2H), 1.21 (s, 3H), 1.22 (s, 3H), 1.42 (m, 4H), 1.84 (s, 4H), 1.98 (s, 3H), 2.03 (s, 3H), 2.08 (m, 2H), 2.15 (s, 3H), 2.17 (s, 3H), 2.43 (t, 2H), 2.51 (s, 4H), 2.70 (s, 1H), 3.99 (d, 6.7 Hz, 1H), 4.22 (d, 8.0 Hz, 1H), 4.29 (d, 8.0 Hz, 1H), 4.97 (d, 8.8 Hz, 1H), 5.51 (m, 2H), 5.84 (d, 6.8 Hz, 1H), 6.13 (m, 1H), 6.28 (s, 1H), 7.07–7.26 (m, 5H), 7.39–7.56 (m, 3H), 8.06 (d, 2H); $^{13}$C NMR (62.5 MHz, CDCl$_3$) δ 10.63, 14.92, 20.64, 20.86, 21.03, 21.61, 22.36, 24.53, 25.74, 28.38, 30.77, 33.30, 33.94, 35.38, 43.21, 46.57, 56.32, 70.99, 71.23, 72.93, 75.16, 76.14, 76.82, 80.54, 83.89, 125.68, 128.21, 128.39, 128.97, 130.24, 133.46, 134.09, 137.80, 142.14, 165.62, 168.76, 170.19, 170.32, 170.76, 171.62, 201.34.

EXAMPLE 27

Cytotoxicity Evaluation

Taxoids, thus synthesized, were evaluated for their cytotoxicity against human tumor cell line, A2780 (ovarian carcinoma), A2780-DX5 (ovarian carcinoma resistant to doxorubicin), MCF7 (mammary carcinoma) or MCF7-R (mammary carcinoma cells resistant to doxorubicin), after 72 hours drug exposure according to the methods of Skehon, et al., "J. Nat. Cancer Inst. 82, 1107, 1990". The results are shown in Table 1. The cytotoxicities of paclitaxel, docetaxel and doxorubicin are also listed for comparison. Lower numbers indicate higher potency. The data represent the means values of at least three separate experiments. Lower numbers indicate stronger cytotoxicity. As Table 1 shows, the taxoids of this invention possess about 1,000 times less cytotocity than paclitaxel against ovarian and breast cancer cells. Low cytotocitiy is preferred for ideal MDR reversal agents.

TABLE 1

| Taxoid | A2780[a] (ovarian) | A2780-DX5[a] (ovarian) | MCF7[a] (breast) | MCF7-R[a] (breast) |
|---|---|---|---|---|
| Paclitaxel | 2.7 | 547 | 1.7 | 850 |
| Doxorubicin | 5.0 | 357 | 17 | 1,890 |
| SB-RA-110 | >10,000 | >10,000 | >10,000 | >10,000 |
| SB-RA-2001 | 2,600 | 3,800 | 2,000 | 5,000 |
| SB-RA-30001 | — | — | 5,300 | 11,000 |
| SB-RA-30011 | 6,300 | 6,800 | 4,700 | 8,000 |
| SB-RA-30012 | — | — | >10,000 | >10,000 |
| SB-RA-30021 | 5,700 | 5,300 | 4,900 | 5,000 |
| SB-RA-31011 | — | — | 11,000 | >10,000 |
| SB-RA-31012 | — | — | >10,000 | >10,000 |
| SB-RA-4001 | 8,000 | 10,000 | 8,500 | >10,000 |
| SB-RA-4102 | — | — | >10,000 | >10,000 |

[a]The concentration of compound which inhibit 50% (IC50, nM) of the growth of human tumor cell line.

Assessment of cytotoxicity, i.e., cell growth inhibition, was determined according to the methods of Skehan, et al. as discussed in J. Nat. Cancer Inst. 82, 1107, 1990. Briefly, cells were plated between 400 and 1200 cells/well in 96 well plates and incubated at 37° C. for 15–18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 h incubation, 100 mL of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL) was added to each well. Following a 5 minute incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

EXAMPLE 28

Activity of Taxoids as MDR Agents

Taxoids, thus synthesized, were evaluated in combination with either paclitaxel or doxorubicin for their cytostatic activity against the drug-resistant breast cancer cells MCF7-R. As shown in Example 27, these taxoids only possess weak cytotoxicity (>2 μM level IC$_{50}$ values) against drug-sensitive and drug-resistant cancer cells. However, these taxoids when used in combination with paclitaxel at 1 or 3 μM concentration decreased the IC$_{50}$ of paclitaxel 20~100-fold, i.e, from 860 to 42~1.6, a reduction of 95~99.8% as shown in TABLE 1. For the IC$_{50}$ vaues, the lower number indicates stronger cytotoxicity and for the % IC$_{50}$ reduction, a larger number shows higher MDR reversal activity. Similarly, the taxoid reversal agents (1 μM SB-RA-30011) enhanced the tumor growth inhibitory activity of doxorubicin by 92% as shown in Table 2.

Consequently, in the presence of these taxoids, paclitaxel and doxorubicin can recover their excellent inhibitory activities against the drug-resistant cancer cells MCF7-R (paclitaxel and doxorubicin possess only weak cytotoxicity, i.e., IC$_{50}$=860 nM and 1,890 nM, respectively, against MCF7-R as shown in TABLEs 1 and 2). It has been proven in these laboratories that the observed remarkable enhancement of paclitaxel's cytotoxicity of against MCF7-R is ascribed to the market increase in the uptake of paclitaxel in MCF7-R cancer cells in the presence of these taxoid reversal agents using a radiolabeled paclitaxel. These results clearly show that these taxoids possess outstanding MDR reversal activity.

TABLE 2

| Taxoid | IC$_{50}$ (nM) | % IC$_{50}$ reduction |
|---|---|---|
| Paclitaxel | 860 | — |
| Doxorubicin | 1,890 | — |
| SB-RA-30001 + Paclitaxel[a] | 21 | 97.5 |
| SB-RA-30011 + Paclitaxel[a] | 36 | 96 |
| SB-RA-30011 + Doxorubicin[a] | 160 | 92 |
| SB-RA-30012 + Paclitaxel[a] | 5.8 | 99.3 |
| SB-RA-30021 + Paclitaxel[a] | 33 | 96 |
| SB-RA-31011 + Paclitaxel[a] | 1.6 | 99.8 |
| SB-RA-31012 + Paclitaxel[a] | 2.6 | 99.7 |
| SB-RA-4001 + Paclitaxel[a] | 42 | 95 |
| SB-RA-4102 + Paclitaxel[a] | 2.7 | 99.7 |

[a]Treatment consists of concurrent exposure of MCF7-R cells to paclitaxel (or doxorubicin) in the presence or absence of the taxoid reversing agent (1 μM) for 72 h in vitro.

We claim:
1. A taxoid of the formula (I)

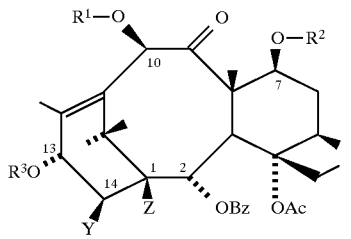

wherein
R$^1$, R$^2$ or R$^3$ represents a radical of the formula R$^4$-(A)$_k$-(R$^5$)$_m$-(B)$_n$ or R$^7$;

R$^4$ is an alkyl radical containing 1 to 10 carbon atoms, an alkenyl radical containing 2 to 10 carbon atoms, or an alkynyl radical containing 2 to 10 carbon atoms, a cycloalkyl radical containing 3 to 10 carbon atoms, a heterocycloalkyl radical containing 3 to 10 carbon atoms, a cycloalkenyl radical containing 3 to 10 carbon atoms, a heterocycloalkenyl radical containing 3 to 10 carbon atoms, a polycycloalkyl radical containing 6 to 20 carbon atoms, an aryl radical containing 6 to 20 carbons, a heteroaryl radical containing 3 to 20 carbon atoms; said cycloalkyl, said heterocycloalkyl, said cycloalkenyl, said heterocycloalkenyl, said polycycloalkyl, said aryl, said heteroaryl radicals being optionally substituted with one or more halogen, hydroxyl, alkoxy, aryloxy, heteroaryloxy, amino, alkylamino, dialkylamino, mercapto, alkylthio, arylthio, heteroarylthio, cyano, carboxyl, akoxycarbonyl the alkyl portion of which containing 1 to 15 carbon atoms, aryloxycarbonyl the aryl portion of which containing 6 to 20 carbons atoms, or heteroaryloxycarbonyl the heteroaryl portion of which containing 3 to 15 carbon atoms;

A is an oxygen, sulfur, or —NR$^6$-radical in which R$^6$ is a hydrogen or R$^4$, R$^5$ is an alkylidene radical containing 1 to 15 carbons, alkenylidene radical containing 2 to 15 carbons, alkynylidene radical containing 2 to 15 carbons;

B is a carbonyl, —OC(O)— or —NR$^6$-radical;

k, m, and n are numbers selected from 0 and 1, however, k, m, and n are not 0 at the same time;

R$^7$ is a hydroxy protecting group, an acyl radical containing 1 to 20 carbons, carbamoyl group, N-substituted carbamoyl radical containing 1 to 20 carbons, or N,N-disubstituted carbamoyl radical containing 2 to 40 carbon, R$^6$ is a hydrogen or R$^4$, R$^7$ is a hydroxy protecting group, an acyl radical containing 1 to 20 carbons, carbamoyl group, N-substituted carbamoyl radical containing 1 to 20 carbons, or N,N-disubstituted carbamoyl radical containing 2 to 40 carbon;

wherein R$^1$, R$^2$, and R$^3$ are not R$^7$ at the same time R$^1$, R$^2$ and R$^3$ are not H at the same time;

Y is a hydrogen, a hydroxyl, or R$^1$O-radical wherein R1 is defined above;

Z is a hydroxyl radical;

Y and Z can be connected to form a cyclic structure.

2. A taxoid according to claim 1, wherein
R$^1$ is a radical further comprising formula R$^{4\#}$-(A)$_k$-(R$^5$)$_m$-(B)$_n$, wherein R$^{4\#}$ is an aryl radical containing 6 to 20 carbons or heteroaryl radical containing 3 to 20 carbon atoms, said aryl or heteroaryl radical substituted by one or more cycloalkyl radical containing 3 to 10 carbon atoms, cycloalkenyl radical containing 3 to 10 carbon atoms, polycycloalkyl radical containing 6 to 20 carbon atoms, said cycloalkyl, said cycloalkenyl, said polycycloalkyl, said aryl, said heteroaryl radicals being optionally substituted with one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl the alkyl portion of which containing 1 to 15 carbon atoms, aryloxycarbonyl the aryl portion of which containing 6 to 20 carbon atoms, or heteroaryloxycarbonyl the heteroaryl portion of which containing 3 to 15 carbon atoms.

3. A taxoid according to the claim 1, wherein
R$^7$ is a hydroxyl protecting group selected from methoxylmethyl (MOM), methoxyethyl (MEM), 1-ethoxyethyl (EE), benzyloxymethyl, (β-trimethylsilyethoxyl)methyl, tetrahydropyranyl, 2,2,2-trichloroethoxylcarbonyl (troc), benzyloxycarbonyl (Cbz), tert-butoxycarbonyl (t-Boc), 9-fluorenylmethoxycarbonyl (Fmoc), 2,2,2-trichloroethoxymethyl, trimethylsilyl, triethylsily (TES), tripropylsilyl, dimethylethylsilyl, (tert-butyl) dimethylsilyl (TBS), diethylmethylsilyl, dimethylphenylsilyl and diphenylmethylsilyl, or an acyl radical selected from acetyl, chloroacetyl, dichloroacetyl, trichloroacetyl, trifluoroacetyl, propanoyl, butanoyl, pentanoyl, hexanoyl, heptanoyl, cyclohexanecarbonyl, octanoyl, nonanoyl, decanoyl, undecanoyl, dodecanoyl, benzoyl, phenylacetyl, naphthalenecarbonyl, indoleacetyl, cyclopropanecarbonyl, fluorobenzoyl, chlorobenzoyl, azidobenoyl, 2-propenoyl, 2-butenoyl, 2-methyl-1-propenoyl, 2-methyl-2-butenoyl, 3-methyl-2-butenoyl readical, or an N-substituted or N,N-disubstituted carbamoyl radical selected from N-methylcarbamoyl, N-ethylcarbamoyl, N-propylcarbamoyl, N-isopropylcarbamoyl, N-butylcarbamoyl, N-pentylcarbamoyl, N-hexylcarbamoyl, N,N-diemthylcarbamoyl, N,N-diethylcarbamoyl, N,N-dipropylcarbamoyl, N,N-dibutylcarbamoyl, pyrrolidine-N-carbonyl, piperidine-N-carbonyl, morpholine-N-carbonyl.

4. A taxoid according to claim 1, wherein
Y and Z are connected to form a carbonate, thiocarbonate, sulfate, sufite, ketal, or acetal.

5. A taxoid according to the claim 1, wherein
R$^4$ is an alkyl radical selected from methyl, ethyl, propyl, isopropyl, butyl, isobutyl, tert-butyl, pentyl, isopentyl, neopentyl, hexyl, heptyl, octyl, nonyl, decyl, cyclohexylmethyl, cyclohexylethyl, benzyl, phenylethyl, phenylethyl, cyclopropyl, cyclobutyl, cyclopentyl, cyclohexyl, cycloheptyl, cyclooctyl, and adamantyl, or an alkenyl radical selected from ethenyl, propenyl, butenyl, pentenyl, hexenyl, heptenyl, octenyl, nonenyl, decenyl, 2-phenylethenyl, 2-furylethenyl, 2-pyrrolylethenyl, 2-pyridylethenyl, 2-thienylethyl, or an unsubstituted or substituted alkynyl radical selected from ethynyl, propynyl, butynyl, pentynyl, hexynyl, heptynyl, octynyl, nonynyl, decynyl, or an aryl radical selected from phenyl, tolyl, methoxyphenyl, dimethoxyphenyl, fluorophenyl, trifluoromethylphenyl, chlorophenyl, dimethylaminophenyl, chlorophenyl, acetylphenyl, pivaloylphenyl, benzoylphenyl, methoxylcarbonylphenyl, tert-butoxycarbonylphenyl, naphthyl, methoxynaphthyl, chloronaphthyl, acetylnaphthyl, benzoylnaphthyl, anthracenyl, phenanthrenyl, or a heteroaryl radical selected from furyl, pyrrolyl, pyridyl, thienyl, benzofuryl, benzopyrrolyl, benzothienyl, quinolinyl, indolyl, N-acetylindolyl, N-methylindolyl, N-allylindolyl, or a cycloalkenyl radical selected from cyclopropyl, cyclopentenyl, cyclohexenyl and cycloheptenyl, or a heterocycloalkyl selected from oxiranyl, pyrrolidinyl, piperidinyl, morpholinyl, tetrahydrofuryl, and tetrahydropyranyl, or a heterocycloalkenyl radical selected from dihydrofuryl, dihydropyrrolyl, dihydropiranyl, dihydropyridyl;

$R^6$ is a hydrogen or $R^4$.

6. A taxoid according to the claim 1, wherein
$(A)_k-(R^5)_m-(B)_n$ is an α-, β- or ω-hydroxyalkanoic acid residue, α-, β-, or ω-mercaptoalkanoic acid residue, or α-, β-, or ω-amino acid residue, wherein k=n=1
or ω-hydroxyalkyl, ω-mercaptoalkyl, or ω-aminoalkyl residue, wherein k=1 and n=0.

7. A taxoid according to the claim 1, wherein
$R^1$, $R^2$ or $R^3$ is selected from 3-(benzoylphenyl)-2-propenoyl, 3-naphthyl-2-propenoyl, 3-biphenyl-2-propenoyl, 3-(phenoxyphenyl)-2-propenoyl, 3-(methoxyphenyl)-2-propenoyl, 3-(ethoxyphenyl)-2-propenoyl, 3-(isopropoxyphenyl)-2-propenoyl, 3-(tert-butoxyphenyl)-2-propenoyl, 3-(isopropylphenyl)-2-propenoyl, 3-(tert-butylphenyl)-2-propenoyl, 3-(trimethylsilylphenyl)-2-propenoyl, 3-anthracenyl-2-propenoyl, 3-phenanthrenyl-2-propenoyl, (benzoylphenyl)acetyl, naphthylacetyl, indoleacetyl, (N-acetyl)indoleacetyl, 3-(benzoylphenyl)propanoyl, 3-naphthylpropanoyl, 3-(biphenyl)propanoyl, 3-(phenoxyphenyl)propanoyl, 3-(methoxyphenyl)propanoyl, 3-(ethoxyphenyl)propanoyl, 3-(isopropoxyphenyl)propanoyl, 3-(tert-butoxyphenyl)propanoyl, 3-(isopropylphenyl)propanoyl, 3-(tert-butylphenyl)propanoyl, 3-(trimethylsilylphenyl)propanoyl, 4-(benzoylphenyl)butanoyl, 4-naphthylbutanoyl, 5-(benzoylphenyl)pentanoyl, 5-naphthylpentanoyl, 6-(benzoylphenyl)hexanoyl, 6-naphthylhexanoyl, 3-(anthracenyl)propanoyl, 4-(anthracenyl)butanoyl, 5-(anthracenyl)pentanoyl, 6-(anthracenyl)hexanoyl, 3-(phenanthrenyl)propanoyl, 4-(phenanthrenyl)butanoyl, 5-(phenanthrenyl)pentanoyl, 6-(phenanthrenyl)hexanoyl, (benzoylphenyl)methyl, naphthylmethyl, 2-(benzoylphenyl)ethyl, 3-(benzoylphenyl)propyl, 3-naphthylpropyl, 4-(benzoylphenyl)butyl, 4-naphthylbutyl, 5-(benzoylphenyl)pentyl, 5-naphthylpentyl, 6-(benzoylphenyl)hexyl, 6-naphthylhexyl, 3-(anthracenyl)propyl, 4-(anthracenyl)butyl, 5-(anthracenyl)pentyl, 6-(anthracenyl)hexyl, 3-(phenanthrenyl)propyl, 4-(phenanthrenyl)butyl, 5-(phenanthrenyl)pentyl, 6-(phenanthrenyl)hexyl.

8. A taxoid according to the claim 1, wherein
Y is an $R^1O$ radical;
$R^1$ is selected from 3-(benzoylphenyl)-2-propenoyl, 3-naphthyl-2-propenoyl, 3-biphenyl-2-propenoyl, 3-(phenoxyphenyl)-2-propenoyl, 3-(methoxyphenyl)-2-propenoyl, 3-(ethoxyphenyl)-2-propenoyl, 3-(isopropoxyphenyl)-2-propenoyl, 3-(tert-butoxyphenyl)-2-propenoyl, 3-(isopropylphenyl)-2-propenoyl, 3-(tert-butylphenyl)-2-propenoyl, 3-(trimethylsilylphenyl)-2-propenoyl, 3-anthracenyl-2-propenoyl, 3-phenanthrenyl-2-propenoyl, (benzoylphenyl)acetyl, naphthylacetyl, indoleacetyl, (N-acetyl)indoleacetyl, 3-(benzoylphenyl)propanoyl, 3-naphthylpropanoyl, 3-(biphenyl)propanoyl, 3-(phenoxyphenyl)propanoyl, 3-(methoxyphenyl)propanoyl, 3-(ethoxyphenyl)propanoyl, 3-(isopropoxyphenyl)propanoyl, 3-(tert-butoxyphenyl)propanoyl, 3-(isopropylphenyl)propanoyl, 3-(tert-butylphenyl)propanoyl, 3-(trimethylsilylphenyl)propanoyl, 4-(benzoylphenyl)butanoyl, 4-naphthylbutanoyl, 5-(benzoylphenyl)pentanoyl, 5-naphthylpentanoyl, 6-(benzoylphenyl)hexanoyl, 6-naphthylhexanoyl, 3-(anthracenyl)propanoyl, 4-(anthracenyl)butanoyl, 5-(anthracenyl)pentanoyl, 6-(anthracenyl)hexanoyl, 3-(phenanthrenyl)propanoyl, 4-(phenanthrenyl)butanoyl, 5-(phenanthrenyl)pentanoyl, 6-(phenanthrenyl)hexanoyl, (benzoylphenyl)methyl, naphthylmethyl, 2-(benzoylphenyl)ethyl, 3-(benzoylphenyl)propyl, 3-naphthylpropyl, 4-(benzoylphenyl)butyl, 4-naphthylbutyl, 5-(benzoylphenyl)pentyl, 5-naphthylpentyl, 6-(benzoylphenyl)hexyl, 6-naphthylhexyl, 3-(anthracenyl)propyl, 4-(anthracenyl)butyl, 5-(anthracenyl)pentyl, 6-(anthracenyl)hexyl, 3-(phenanthrenyl)propyl, 4-(phenanthrenyl)butyl, 5-(phenanthrenyl)pentyl, 6-(phenanthrenyl)hexyl;

Z is a hydroxyl radical.

9. A taxoid according to claim 1, wherein
$R^4$ is selected from benzoylphenyl, naphthyl, phenoxylphenyl, methoxyphenyl, ethoxyphenyl, isopropoxyphenyl, tert-butoxyphenyl, anthracenyl, phenathrenyl, isopropylphenyl, tert-butylphenyl, trimethylsilylphenyl;

$(A)_k-(R^5)_m-(B)_n$ is a hydroxyalkanoic acid residue selected from hydroxyacetyl, hydroxypropyl, and hydroxybutyl, or a mercaptoalkanoic acid residue selected from mercaptoacetyl, mercaptopropanoyl, mercaptobutanoyl, or an amino acid residue selected from, glycinyl, alanyl, β-alanyl, 4-aminobutanoyl, valyl, leucyl, isoleucyl, methionyl, phenylalanyl, tryptophanyl.

10. A taxoid according to the claim 1, wherein
$R^1$, $R^2$ or $R^3$ is selected from 3-(4-benzoylphenyl)-2-propenoyl, 3-(4-benzoylphenyl)propanoyl, 3-(2-naphthyl)-2-propenoyl, and 3-(2-naphthyl)propanoyl.

11. A taxoid according to the claim 1, wherein
$R^1$, $R^2$ or $R^3$ is selected from 3-(4-benzoylphenyl)-2-propenoyl, 3-(4-benzoylphenyl)propanoyl, 3-(2-naphthyl)-2-propenoyl, and 3-(2-naphthyl)propanoyl;

Y and Z are connected to form a carbonate, thiocarbonate, sulfate, sufite, ketal, or acetal.

12. A taxoid according to claim 1, wherein
$R^1$ and $R^2$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^3$ is a hydrogen or an acetyl radical;

Y is a hydrogen;

Z is a hydroxyl radical.

13. A taxoid according to the claim 1, wherein $R^1$ and $R^2$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^3$ is a hydrogen or an acetal radical;

Y and Z are connected to form a carbonate, thiocarbonate, sulfate, sufite, ketal, or acetal.

14. A taxoid according to the claim 1, wherein $R^1$ and $R^3$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^2$ is a hydrogen or an acetyl radical;

Y is a hydrogen;

Z is a hydroxyl radical.

15. A taxoid according to the claim 1, wherein $R^2$ and $R^3$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

$R^1$ is a hydrogen or an acetyl radical;

Y is a hydrogen;

Z is a hydroxyl radical.

16. A taxoid according to the claim 1, wherein $R^1$, $R^2$ and $R^3$ are selected from 3-(4-benzoylphenyl)-2-propenoyl, 3-(4-benzoylphenyl)propanoyl, 3-(2-naphthyl)-2-propenoyl, and 3-(2-naphthyl)propanoyl;

Y is a hydrogen,

Z is a hydroxyl radical.

17. A pharmaceutical composition having drug-resistance reversal activity comprising the compound of claim 1 and a physiologically acceptable carrier therefor.

18. A method for treating tumors which comprises administrating to a patient an effective amount of paclitaxel or doxorubicin with an effective amount of drug-resistance reversal compound of claim 1.

19. A method according to claim 18, wherein said treatment comprises treating tumors selected from the group consisting of leukemia, melanoma, breast, non-small cell lung, ovarian, renal and colon cancers.

* * * * *

UNITED STATES PATENT AND TRADEMARK OFFICE
CERTIFICATE OF CORRECTION

PATENT NO. : 5,811,452
DATED : September 22, 1998
INVENTOR(S) : Ojima et al.

It is certified that error appears in the above-identified patent and that said Letters Patent is hereby corrected as shown below:

| | |
|---|---|
| In Column 2, Line 14, | delete "non-crytotoxic", and insert therefor --non-cytotoxic--. |
| In Column 3, Line 3, | delete "non-drug resistant", and insert therefor --non-drug-resistant--. |
| In Column 4, Line 52, | delete "branched alkenyl radical containing 2 to 20 carbon", and insert therefor --branched alkynyl radical containing 2 to 10 carbon--. |
| In Column 5, Line 22, | delete "methoxyphenyl dimethoxyphenyl", and insert therefor --methoxyphenyl, dimethoxyphenyl--. |
| In Column 6, Line 59, | delete "-2-propenoyl 3-(", and insert therefor ---2-propenoyl, 3-(--. |
| In Column 7, Line 55, | delete "radical", and insert therefor --radical.--. |
| In Column 8, Line 4, | delete "radical", and insert therefor --radical.--. |
| In Column 9, Line 67, | delete "n defined above", and insert therefor --n are defined above--. |
| In column 15, 1st paragraph | delete "position of VII", and insert therefor --position of VIII--. |

UNITED STATES PATENT AND TRADEMARK OFFICE
CERTIFICATE OF CORRECTION

PATENT NO. : 5,811,452
DATED : September 22, 1998
INVENTOR(S) : Ojima et al.

It is certified that error appears in the above-identified patent and that said Letters Patent is hereby corrected as shown below:

In Column 23, Line 3, delete "is to necessarily", and insert therefor --is not necessarily--.

In Column 31, Line 67, delete "$[\alpha]_D$", and insert therefor --$[\alpha]^{20}_D$--.

In Column 34, Line 59, delete "1//1", and insert therefor --1/1--.

Signed and Sealed this

Sixteenth Day of March, 1999

Attest:

Attesting Officer

Q. TODD DICKINSON

Acting Commissioner of Patents and Trademarks